United States Patent [19]

Oshiro et al.

[11] Patent Number: 4,792,628
[45] Date of Patent: Dec. 20, 1988

[54] INDANE DERIVATIVES AND SALTS THEREOF

[75] Inventors: Yasuo Oshiro; Hiraki Ueda; Kazuyuki Nakagawa, all of Tokushima, Japan

[73] Assignee: Otsuka Pharmaceutical Co., Ltd., Tokyo, Japan

[21] Appl. No.: 39,779

[22] Filed: Apr. 16, 1987

Related U.S. Application Data

[63] Continuation of Ser. No. 585,607, Mar. 2, 1984, abandoned.

[30] Foreign Application Priority Data

Mar. 4, 1983 [JP] Japan ................... 58-36429
Oct. 11, 1983 [JP] Japan ................... 58-190269
Dec. 29, 1983 [JP] Japan ................... 58-245875

[51] Int. Cl.$^4$ ........................... C07C 87/457
[52] U.S. Cl. ........................... 564/428; 546/206; 564/91; 564/92; 564/99; 564/158; 564/184; 564/211; 564/222; 564/300; 564/307; 564/374; 564/378; 564/387; 564/389
[58] Field of Search ................. 564/300, 307, 428, 91, 564/92, 99, 158, 184, 211, 222, 374, 378, 387, 389; 514/647, 657; 546/206

[56] References Cited

U.S. PATENT DOCUMENTS 2,916,490 12/1959 Schenck et al. ............. 564/428
3,637,740 1/1972 Sarges ........................ 564/428
3,709,996 1/1973 Gittos et al. .................. 514/657

OTHER PUBLICATIONS

Deana et al "2-(Aminomethyl)phenols, A New Class of Saluretic Agents", *J. of Med. Chem.*, 1983, vol. 26, No. 4, pp. 580–585.

*Primary Examiner*—Glennon H. Hollrah
*Assistant Examiner*—John A. Sopp
*Attorney, Agent, or Firm*—Finnegan, Henderson, Farabow, Garrett & Dunner

[57] ABSTRACT

Indane derivatives and their salts represented by the general formula (1),

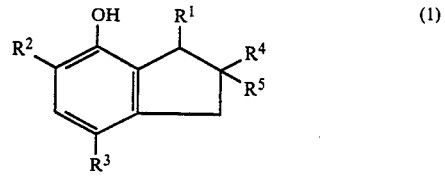

wherein $R^1$ is an amino group which may have lower alkyl groups as the substituents, a hydroxylimino group, an alkanoylamino group having 1 to 10 carbon atoms which may have halogen atoms as the substituents, a lower alkylsulfonylamino group, a phenylsulfonylamino group which may have lower alkyl groups as the substituents on the phenyl ring, a benzoylamino group having lower alkyl groups as the substituents on the phenyl ring, and a phenyl-lower alkylamino group having a hydroxyl groups or a lower alkyl groups as the substituents on the phenyl ring, $R^2$ is a hydrogen atom, a lower alkyl group, a halogen atom, a nitro group, an amino group, an amino-lower alkyl group, a lower alkanoylamino group, a lower alkanoylamino-lower alkyl group which may have halogen atoms as the substituents, a lower alkylthio group, a 1-piperidinesulfonyl group, or a lower alkenyl group; $R^3$ is a hydrogen atom, a lower alkyl group, or a halogen atom; $R^4$ and $R^5$ are the same or different from each other, and are each a hydrogen atom, or a lower alkyl group; provided that when $R^1$ is a hydroxylimino group, then $R^2$ and $R^3$ should not be hydrogen atoms at the same time.

The indane derivatives and their salts are useful as preventive and curative agents for various diseases and disorders caused by the excessive formation and accumulation of the active oxygen radicals and the peroxidized substances in the living body, and/or the defects of phylaxis mechanisms of the living body, for example anti-arreriosclerotic agents, carcinogenesis preventive agents, carcinostatic agents, anti-inflammatory agents, analgesics, autoimmune disease curative agents, platelets aggregation inhibitory agents, hypotensive agents, anti-hyperlipemic agents, retinosis of immature infant and cataract preventive and curative agents.

The indane derivatives and their salts are also useful as antioxidants for oils and fats being contained in processed foods.

35 Claims, 1 Drawing Sheet

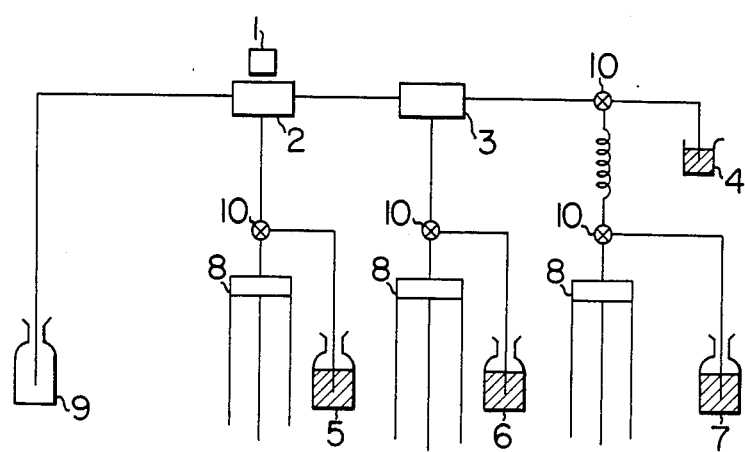

INDANE DERIVATIVES AND SALTS THEREOF

This application is a continuation division, for application Ser. No. 06/585,607, filed Mar. 2, 1984, now abandoned.

FIELD OF THE INVENTION

The present invention relates to novel indane derivatives and salts thereof having excellent anti-inflammatory, hypotensive, gastric juice secretioinhibitory actions, as well as having immunosupressive action and further having excellent activities for improving anoxemic and hypoxic symptoms and syndromes accompanied therewith. Thus the novel indane derivatives and salts thereof are useful as anti-inflammatory agents, hypotensive agents, improving agents for treating anoxemic and hypoxic symptoms and syndromes accompanied therewith, cerebral activators, amnesia curative agents, presbyophrenia curative agents treating agents for breathing arrest and improving agents for hypoxia accompanied with potassium cyanide poisoning, as well as they are useful as prophylactics for arrhythmia and heart failure caused by hypoxia.

PRIOR ART

Oxygen is essential to the living body for sustaining the life through release of energies and metabolisms. Oxygen is converted into so-called "active oxygen radicals", for example oxygen anion radical, peroxide ion, hydroxy radical, etc. in various biochemical reactions, such as energy releasing ractions, enzymatic reactions, and other reactions caused by exposures of ultraviolet rays and various radiations.

The active oxygen radicals are indeed useful for the actions of oxygenase and of phagocytosis carried out by leucocytes. On the other hand, the active oxygen radicals promote peroxidation reaction of unsaturated fatty acids, such as oleic acid, linoleic acid, linolenic acid and arachidonic acid, etc. These unsaturated fatty acid are existing abundantly in the living body, and are the main constituents of the biomembranes. The peroxidation reaction of the unsaturated fatty acids produce peroxidized substances such as peroxidized lipids. Similar to the active oxygen radicals, said peroxidized substances also produce alkoxy radicals and hydroxy radicals which will attack the biomembranes and will result disorder of the biomembranes and deactivation of various usefll enzymes working in the living body. ["TAI-SHA" (Metabolisms), Vol. 15, No. 10, (1978), Special issue of active oxygen].

On the other hand, there are existing some other enzymes, such as superoxide dismutase (hereinafter referred to as SOD), catalase, glutathion peroxidase, etc. in the living body, these enzymes prevent the deactivation of metabolism from attack of the active oxygen radicals. Additionally, there are existing several vitamins, such as tocopherols (vitamin E groups) having antioxidative activities in the living body.

Generally, the normal homeostasis of the living body is sustained by the actions of these enzymes and vitamins having antioxidative activities. However, sometimes the phylaxis mechanisms of the living body being suitably maintained by the actions of these enzymes and vitamins may be defected by certain reasons, and the formation of the active oxygen radicals in an amount exceeds the ability of the phylaxis mechanism of the living body, as well as the formation and accumulation of the peroxidized substances are observed. In such cases that the phylaxis mechanism of the living body is defected, then several severe disorders such as various diseases caused by the aggregation of the platelets, inflammations, disorder of the liver, arteriosclerosis, hemolysis, senescene or presbyopherenia, retinosis, disorder of the lungs, disorders of the heart and the lungs caused by the action of certain drugs, ischemic coronary heart disease and the like will be occured accompanied with the progressive chain reactions of the peroxidation.

Hitherto, compounds having actions for scavenging the active oxygen radicals which are considered to be the main factors of the above-mentioned various diseases, and for preventing or lowering the formation and accumulation of the peroxidized substances in the living body were known and called as antioxidants. A number of studies on prophylaxis and curative effects by using these antioxidants have been reported in related literatures. As to enzymatic preparations containing SOD and other enzymes as mentioned previously are reported in "SUPEROXIDE TO IGAKU" (Superoxide and Medicine) by Yoshihiko Ohyanagi, pages 137 to 141, (1981), published from Kyoritsu Publishing Co., Ltd. Further, as to other antioxidants, such as butylhydroxytoluene (BHT), butylhydroxyanisol (BHA), α-tocopherol (vitamin E) and others are reported in "IYAKU JOURNAL" (Pharmaceutical Journal), Vol. 19, No. 12, pages 2351 to 2359, (1983) by Makoto Mino, and Hidetaka Tanaka; Ibid. Vol. 19, No. 5, pages 909 to 914, (1983) by Toshihiko Suematsu.

BRIEF DESCRIPTION OF THE DRAWING

FIG. 1 is a flow diagram showing an apparatus for determining antioxidative activity of indane derivatives of the present invention and reference compound.

Wherein, numeral 1 is a photocounter, numeral 2 is a cell, numeral 3 is a mixer, numeral 4 is a test compound solution, numeral 5 is a Luminol (chemoluminescent) solution, numeral 6 is a FCS (catalyst) solution, numeral 7 is a buffer solution for washing, numeral 8 is a syringe and numeral 9 is a bottle for receiving drainage, and numeral 10 is a stop-valve.

BRIEF SUMMARY OF THE INVENTION

The indane derivatives and their salts of the present invention have actions for scavenging the active oxygen radicals and for preventing or lowering the formation of the peroxidized lipids in the living body. Therefore, the indane derivatives and their salts of the present invention are useful as the preventive and curative agents for various diseases and disorders caused by the excessive formation and accumulation of the active oxygen radicals, and the peroxidized substances such as peroxidized lipids in the living body, and/or the defects of phylaxis mechanism of the living body, for example anti-arteriosclerotic agents, carcinogenesis preventive agents, carcinostatic agents, anti-inflammatory agents, analgesics, autoimmune disease curative agents, platelets aggregation inhibitory agents, hypotensive agents, anti-hyperlipemic agents, retinosis of immature infant and cataract preventive and curative agents.

The indane derivatives and their salts are also useful as antioxidants for oils and fats being contained in processed foods.

An object of the present invention is to provide novel indane derivatives and their salts as represented by the general formula (1) mentioned below, having excellent anti-inflammatory, hypotensive, gastric juice secretioinhibitory actions, immunosupressive actions and activities for improving anoxemic and hypoxic symptoms and syndromes accompanied therewith.

Another object of the present invention is to provide processes for preparing novel indane derivatives and their salts represented by the general formula (1).

Further object of the present invention is to provide a pharmaceutical composition containing indane derivatives represented by the general formula (1) as the active ingredient.

DETAILED DESCRIPTION

The indane derivatives and their salts of the present invention are novel which have not been known in any related literature up to the date, and are represented by the general formula (1) ss follows:

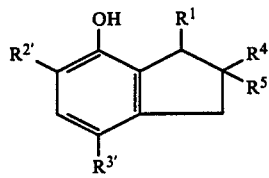

wherein $R^1$ is an amino group which may have lower alkyl groups as the substituents, a hydroxylimino group, an alkanoylamino group having 1 to 10 carbon atoms which may have halogen atoms as the substituents, a lower alkylsulfonylamino group, a phenylsulfonylamino group which may have lower alkyl groups as the substituents on the phenyl ring, a benzoylamino group having lower alkyl groups as the substituents on the phenyl ring, and a phenyl-lower alkylamino group having a hydroxyl groups or a lower alkyl groups as the substituents on the phenyl ring; $R^2$ is a hydrogen atom, a lower alkyl group, a halogen atom, a nitro group, an amino group, an amino-lower alkyl group, a lower alkanolylamino group, a lower alkanoylamino-lower alkyl group which may have halogen atoms as the substituents, a lower alkylthio group, a 1-piperidinesulfonyl group, or a lower alkenyl group; $R^3$ is a hydrogen atom, a lower alkyl group, or a halogen atom; $R^4$ and $R^5$ are the same or different from each other, and are each a hydrogen atom, or a lower alkyl group; provided that when $R^1$ is a hydroxylimino group, then $R^2$ and $R^3$ should not be hydrogen atoms at the same time.

In the present specification, the symbols of $R^1$, $R^2$, $R^3$, $R^4$ and $R^5$ are exemplified more specifically as follows.

As to the lower alkyl group, a straight chain- or branched chain-alkyl group having 1 to 6 carbon atoms, such as methyl, ethyl, propyl, isopropyl, butyl, tert-butyl, pentyl, hexyl, 1-methylpropyl, 2-methylpropyl, 1,1-dimethylpropyl, 1-methylbutyl, 2-methylbutyl, 3-methylbutyl, 2,2-dimethylpropyl, 2,3-dimethylbutyl, 1-methylpentyl, 1,1-dimethylbutyl and 1-ethylbutyl groups can be exemplified.

As to the halogen atom, fluorine, chlorine, bromine and iodine atoms can be exemplified.

As to the amino group which may have lower alkyl groups as the substituents, an amino group which may have straight chain- or branched chain-alkyl groups having 1 to 6 carbon atoms as the substituents, such as amino, N-methylamino, N-ethylamino, N-propylamino, N-isopropylamino, N-butylamino, N-tert-butylamino, N-pentylamino, N-hexylamino, N,N-dimethylamino, N,N-dipropylamino, N,N-dibutylamino, N,N-dihexylamino, N-methyl-N-ethylamino, N-methyl-N-isopropylamino, N-methyl-N-tert-butylamino, N-methyl-N-pentylamino, N-ethyl-N-pentylamino and N-tert-butyl-N-ethylamino groups can be exemplified.

As to the alkanoylamino group having 1 to 10 carbon atoms which may have halogen atoms as the substituents, a straight chain- or branched chain-alkanoylamino group having 1 to 10 carbon atoms which may have halogen atoms as the substituents, such as formylamino, acetylamino, propionylamino, butyrylamino, tert-butylcarbonylamino, pentanoylamino, hexanoylamino, heptanoylamino, octanoylamino, nonanoylamino, decanoylamino, 2,2,2-trifluoroacetylamino, 2,2,2-trichloroacetylamino, 2-chloroacetylamino, 2-bromoacetylamino, 2-fluoroacetylamino, 2-iodoacetylamino, 2,2-difluoroacetylamino, 2,2-dibromoacetylamino, 3,3,3-trifluoropropionylamino, 3,3,3-trichloropropionylamino, 3-chloropropionylamino, 2,3-dichloropropionylamino, 4,4,4-trichlorobutyrylamino, 4-fluorobutyrylamino, 5-chloropentanoylamino, 3-chloro-2-methylpropionylamino, 6-bromohexanoylamino, 7-iodoheptanoylamino, 8-fluorooctanoylamino, 9-chlorononanoylamino, 10-bromodecanoylamino, 5,6-dibromohexanoylamino and 2,2-dichloroheptanoylamino groups can be exemplified.

As to the lower alkylsulfonylamino group, a straight chain- or branched chain-alkylsulfonylamino group having 1 to 6 carbon atoms, such as methylsulfonylamino, ethylsulfonylamino, propylsulfonylamino, isopropylsulfonylamino, butylsulfonylamino, tert-butylsulfonylamino, pentylsulfonylamino and hexylsulfonylamino groups can be exemplified.

As to the phenylsulfonylamino group which may have lower alkyl groups as the substituents on the phenyl ring, a phenylsulfonylamino group which may have straight chain- or branched chain-alkyl groups having 1 to 6 carbon atoms as the substituents on the phenyl ring, such as hhenylsulfonylamino, 2-, 3- or 4-methylphenylsulfonylamino, 2-, 3- or 4-ethylphenylsulfonylamino, 4-propylphenylsulfonylamino, 3-isopropylphenylsulfonylamino, 2-butylphenylsulfonylamino, 4-hexylphenylsulfonylamino, 3-pentylphenylsulfonylamino, 4-tert-butylphenylsulfonylamino, 3,4-dimethylphenylsulfonylamino, 2,5-dimethylphenylsulfonylamino and 3,4,5-trimethylphenylsulfonylamino groups can be exemplified.

As to the benzoylamino group having lower alkyl groups as the substituents on the phenyl ring, a benzoylamino group which may have straight chain- or branched chain-alkyl groups having 1 to 6 carbon atoms as the substituents on the phenyl ring, such as 2-, 3- or 4-methylbenzoylamino, 2-, 3- or 4-ethylbenzoylamino, 4-propylbenzoylamino, 3-isopropylbenzoylamino, 2-butylbenzoylamino, 4-hexylbenzoylamino, 3-pentylbenzoylamino and 4-tert-butylbenzoylamino groups can be exemplified.

As to the phenyl-lower alkylamino group having hydroxyl groups or lower alkyl groups as the substituents on the phenyl ring, a phenylalkylamino group which may have hydroxy groups or straight chain- or branched chain-alkyl groups having 1 to 6 carbon atoms as the substituents on the phenyl ring, such as 2-, 3- or 4-hydroxybenzylamino, 2-(3-hydroxyphenyl)ethylamino, 1-(2-hydroxyphenyl)ethylamino, 3-(2-hydroxyphenyl)propylamino, 4-(4-hydroxyphenyl)- butylamino, 1,1-dimethyl-2-(3-hydroxyphenyl)ethylamino, 5-(2-hydroxyphenyl)pentylamino, 6-(4-hydroxyphenyl)hexylamino, 2-methyl-3-(4-hydroxyphenyl)propylamino, 2-, 3- or 4-methylbenzylamino, 4-ethylbenzylamino, 4-propylbenzylamino, 3-isopropylbenzylamino, 2-butylbenzylamino, 4-hexylbenzylamino, 3-pentylbenzylamino, 4-tert-butylbenzylamino, 2-(3-methylphenyl)ethylamino, 1-(2-ethylphenylethylamino, 3-(2-propylphenyl)propylamino, 4-(4-butylphenyl)butylamino, 1,1-dimethyl-2-(3-hexylphenyl)ethylamino, 5-(2-pentylphenyl)pentylamino, 6-(4-tert-butylphenyl)hexylamino, 2-methyl-3-(4-methylphenyl)propylamino, 2-methyl-3-hydroxybenzylamino, 3,5-di-tert-butyl-4-hydroxybenzylamino, 3-ethyl-5-hydroxybenzylamino, 4-(2-hydroxy-4-propylphenyl)butylamino, 6-(2,3-dimethyl-4hydroxyphenyl)hexylamino, 3,5-, 3,4- or 2,6-dihydroxybenzylamino, 3,4,5-trihydroxybenzylamino, 3,4-, 2,5- or 2,6-dimethylbenzylamino and 3,4,5-trimethylbenzylamino groups can be exemplified.

As to the amino-lower alkyl group, an aminoalkyl group having a straight chain- or branched chain-alkyl group having 1 to 6 carbon atoms in the alkyl moiety, such as aminomethyl, 2-aminoethyl, 1-aminoethyl, 3-aminopropyl, 4-aminobutyl, 1,1-dimethyl-2-aminoethyl, 5-aminopentyl, 6-aminohexyl and 2-methyl-3-aminopropyl groups can be exemplified.

As to the lower alkanoylamino group, a straight chain- or branched chain-alkanoylamino group having 1 to 6 carbon atoms, formylamino, acetylamino, propionylamino, butyrylamino, tert-butyrylamino, pentanoylamino and hexanoylamino groups can be exemplified.

As to the lower alkanoylamino-lower alkyl group which may have halogen atoms as the substituents, a straight chain- or branched chain-alkyl group having 1 to 6 carbon atoms which is substituted with a straight chain- or brnnched chain-alkanoylamino group having 1 to 6 carbon atoms in the alkanoyl moiety which may have halogen atoms as the substituents such as 2,2,2-trifluoroacetylaminomethyl, 2,2,2-trichloroacetylaminomethyl, 2-chloroacetylaminomethyl, 2-(2-bromoacetylamino)ethyl, 1-(2-fluoroacetylamino)ethyl, 3-(2-iodoacetylamino)propyl, 4-(2,2-difluoroacetylamino)butyl, 1,1-dimethyl-2-(2,2-dibromoacetylamino)ethyl, 5-(3,3,3-trifluoropropionylamino)pentyl, 6-(3,3,3-trichloropropionylamino)hexyl, 2-methyl-3-(3-chloropropionylamino)propyl, 2,3-dichloropropionylaminomethyl, 2-(4,4,4-trichlorobutyrylamino)ethyl, 1-(4-fluorobutyrylamino)ethyl, 3-(5-chloropentanoylamino)propyl, 4-(3-chloro-2-methylpropionylamino)butyl, 1,1-dimethyl-2-(6-bromohexanoylamino)ethyl and 5-(5,6dibromohexanoylamino)pentyl groups can be exemplified.

As to the lower alkylthio group, a straight chain- or branched chain-alkylthio group having 1 to 6 carbon atoms, such as methylthio, ethylthio, propylthio, isopropylthio, uutylthio, tert-butylthio, pentylthio and hexylthio groups can be exemplified.

As to the lower alkenyl group, a straight chain- or branched chain-alkenyl group having 2 to 6 carbon atoms, such as vinyl, allyl, 2-butenyl, 3-butenyl, 1-methylallyl, 2-pentenyl, and 2-hexenyl groups can be exemplified.

The indane derivatives and their salts can be prepared by various processes explained as follows.

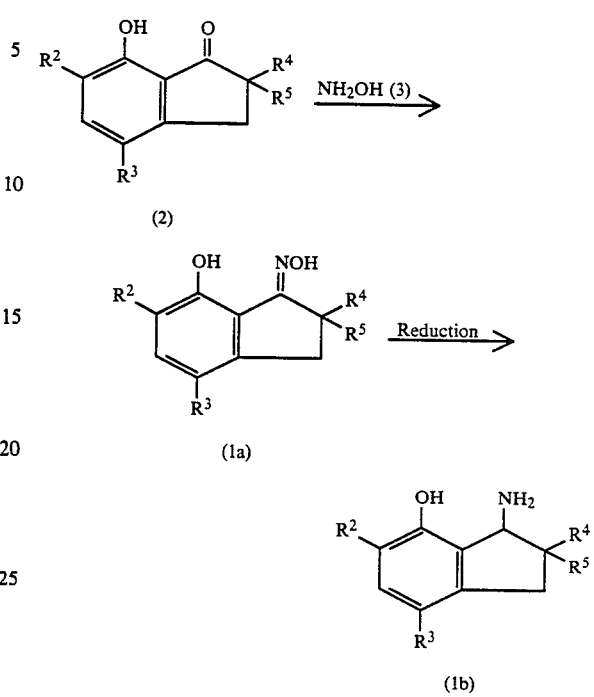

Reaction scheme-1 wherein $R^2$, $R^3$, $R^4$ and $R^5$ are the same as defined above.

The reaction of a known compound (2) with hydroxylamine (3) can be carried out in a suitable inert solvent, in the presence or absence of a basic compound.

As to the basic compound used in this reaction, examples are inorganic basic compounds such as sodium hydroxide, potassium hydroxide, sodium carbonate, potassium carbonate, etc.; and organic basic compounds such as piperidine, pyridine, triethylamine, 1,5-diazabicyclo[4,3,0]nonene-5 (DBN), 1,8-diazabicyclo[5,4,0]undecene-7 (DBU), 1,4-diazabicyclo[2,2,2]octane (DABCO), etc.

As to the inert solvent used in this reaction, any solvent which does not give any adverse effect to the reaction can be used, examples are lower alcohols such as methanol, ethanol, isopropanol, etc.; ethers such as dioxane, tetrahydrofuran, diethyl ether, ethylene glycol monomethyl ether, etc.; aromatic hydrocarbons such as benzene, toluene, xylene, etc., halogenated hydrocarbons such as dichloromethane, dichloroethane, chloroform, carbon tetrachloride, etc.; and polar solvents such as dimethylformamide, dimethyl sulfoxide, hexamethylphosphoryl triamide, etc.

The ratio of the amount of hydroxylamine (3) used to the amount of compound (2) is generally at least an equimolar quantity, preferably an equimolar quantity to 5 times the molar quantity of the latter. The reaction is generally carried out at a room temperature to 200° C., preferably at 50° to 150° C., and is completed in 1 to 10 hours.

The reduction reaction of compound (1a) can be carried out in a suitable solvent in the presence of a catalyst by a catalytic hydrogenation procedure.

As to the solvent used in this catalytic hydrogenation, examples are water, acetic acid, alcohols such as methanol, ethanol, isopropanol, etc.; hydrocarbons such as hexane, cyclohexane, etc.; ethers such as diethylene glycol dimethyl ether, dioxane, tetrahydrofuran, diethyl ether, etc.; esters such as ethyl acetate, methyl acetate, etc.; aprotic polar solvents such as dimethylformamide, etc.

As to the catalyst used in this catalytic hydrogenation, examples are palladium, palladium black, palladium-carbon, platinum, platinum oxide, copper chromite catalyst, Raney nickel, etc. The ratio of the amount of the catalyst used to the amount of compound (1a) is generally 0.02 to equivalent quantity by weight of the latter. The reaction is generally carried out at −20° C. to a room temperature, preferably at 0° C. to a room temperature, under 1 to 10 atmospheric hydrogen pressure, and is generally completed in 0.5 to 10 hours.

The indane derivatives of the present invention can also be prepared by a process as shown in the following reaction scheme-2.

Reaction scheme-2

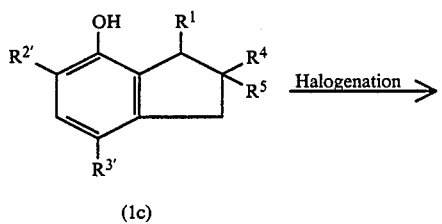

(1c)

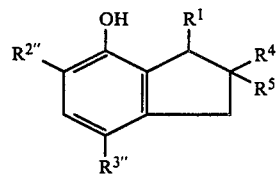

wherein $R^1$, $R^4$ and $R^5$ are the same as defined above; $R^{2'}$ and $R^{3'}$ are the same as defined in $R^2$ and $R^3$ except that they are not halogen atoms; provided that any one of $R^{2'}$ and $R^{3'}$ is a hydrogen atom; $R^{2''}$ and $R^{3''}$ are respectively the same as defined in $R^2$ and $R^3$ provided that at least any one of $R^{2''}$ and $R^{3''}$ is a halogen atom.

The halogenation reaction of compound (1c) is generally carried out in a solvent, in the presence of a common halogenating agent. As to the halogenating agent used in this reaction, any known compound used in halogenating reaction can be used, and examples are halogen molecules such as bromine, chlorine, etc.; iodine monochloride, sulfuryl chloride, and N-halogenosuccinimide such as N-bromosuccinimide, N-chlorosuccinimide. The ratio ff the amount of the halogenating agent used to the amount of compound (1c) is generally an equimolar to 10 times the molar quantity, preferably an equimolar to 5 times the molar quantity of the latter.

As to the solvent used in this halogenating reaction, examples are halogenated hydrocarbons such as dichloromethane, dichloroethane, chloroform, carbon tetrachloride, etc.; acetic acid, propionic acid, water, etc.

The reaction is generally carried out at 0° C. to the boiling point of the solvent used, preferably at 0° to 40° C., and the reaction is generally completed in 1 to 10 hours.

Reaction scheme-3

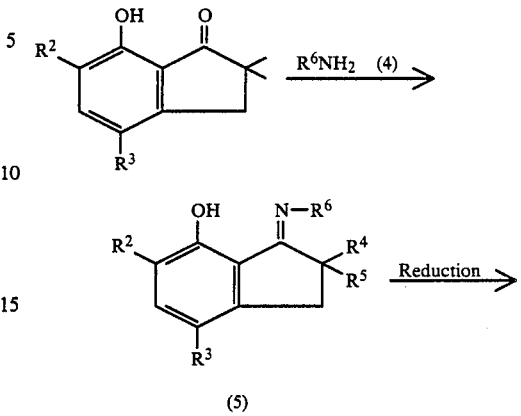

wherein $R^2$, $R^3$, $R^4$ and $R^5$ are the same as defined above; $R^6$ is a hydrogen atom, a lower alkyl group, a lower alkylsulfonyl group, a phenyl-lower alkyl group having hydroxyl group(s) or lower alkyl group(s) as the substituent(s) on the phenyl ring, and a phenylsulfonyl group which may have lower alkyl group(s) as the substituent(s) on the phenyl ring.

The reaction of compound (2) with compound (4) can be carried out in a suitable solvent, in the presence or absence of a dehydrating agent.

As to the solvent used in this reaction, examples are alcohols such as methanol, ethanol, isopropanol, etc.; aromatic hydrocarbons such as benzene, toluene, xylene, etc.; and aprotic polar solvents such as dimethylformamide, dimethylacetamide, N-methylpyrolidone, etc.

As to the dehydrating agent used in this reaction, examples are desiccant which is used in drying a common solvent such as molecular sieve; mineral acids such as hydrogen chloride, sulfuric acid, boron trifluoride, etc.; organic acids such as p-toluenesulfonic acid.

The reaction is generally carried out at a room temperature to 250° C., preferably at 50° to 200° C., and is completed in 1 to 48 hours.

The ratio of the amount of compound (4) used to the amount of compound (2) is generally at least an equimolar quantity, preferably in a large excess quantity.

The amount of the dehydrating agent used in this reaction is a large excess amount in the case of desiccant, and may used a catalytic quantity in the case of acid.

Thus obtained compound (5) contained in the reaction mixture may be subjected to the reduction reaction without separation. The reduction reaction of compound (5) can be carried out by any method known in the art, for example, preferably reduction by using hydrogenation reducing agent. As to the hydrogenation reducing agent, examples are sodium aluminum hydride, sodium borohydride, diborane, etc.

The ratio of the amount of the hydrogenation reducing agent usdd to the amount of compound (5) at least is an equimolar quantity, preferably in the rnnge of an equimolar quantity to 10 times the molar quantity to the latter. In the case of using lithium aluminum hydride as the hydrogenating reducing agent, 2 times the molar quantity thereof is preferably used to the amount of compound (5).

The hydrogenation reducing reaction is generally carried out in a suitable solvent, for example water, lower alcohols such as methanol, ethanol, isopropanol, etc.; ethers such as tetrahydrofuran, diethyl ether, diethylene glycol dimethyl ether (diglyme), etc. at $-60°$ to $50°$ C., preferably at $-30°$ C. to a room temperature, for about 10 minutes to 5 hours. In the case of using lithium aluminum hydride or diborane as the reducing agent, an anhydrous solvent such as diethyl ether, tetrahydrofuran, diglyme may preferably be used.

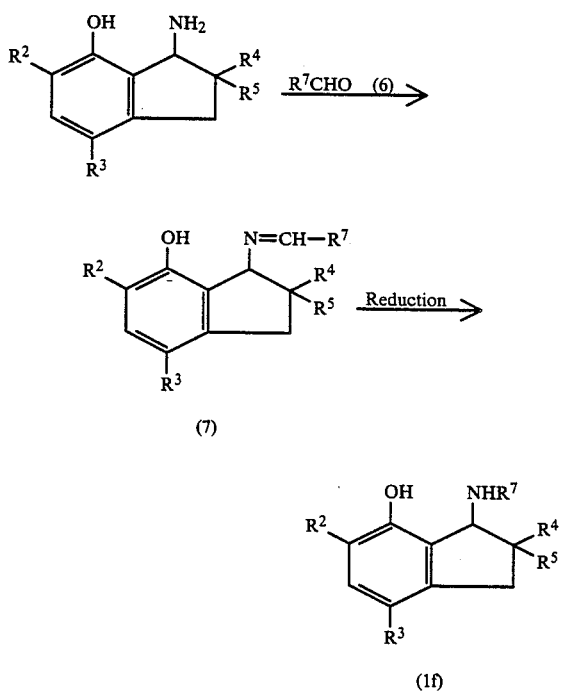

(7)

(1f)

wherein $R^2$, $R^3$, $R^4$ and $R^5$ are the same as defined above; $R^7$ is a phenyl-lower alkyl group having hydroxyl group(s) or lower alkyl group(s) as the substituent(s) on the phenyl ring.

The reaction of compound (1b) with compound (6) can be carried out under the condition similar to that of the reaction of compound (2) with compound (4) in the above-mentioned reaction scheme-3. Further, the reduction of compound (7) can be carried out under the condition similar to that of the reduction of compound (5) in the above-mentioned reaction scheme-3.

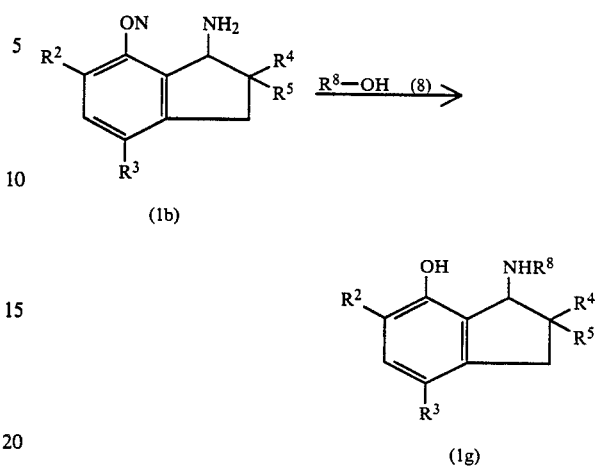

(1b)

(1g)

wherein $R^2 R^3$, $R^4$ and $R^5$ are the same as defined above; and $R^8$ is an alkanoyl group having 1 to 10 carbon atoms which may have halogen atom(s) as the substituent(s), or a benzoyl group having lower alkyl group(s) as the substituent(s) on the phenyl ring.

The reaction of compound (1b) with compound (8) is carried out by a method of usual amide bond formation reaction. In this case, said compound (8), i.e., carboxylic acid is used as in the form of activated compound.

The amide bond formation reaction can be carried out by applying reaction conditions used in common amide bond formation reaction. For example, (a) a mixed acid anhydride method, that is a method by reacting a carboxylic acid (8) with an alkyl haloformate to obtain a mixed acid anhydride, then reacting said mixed acid anhydride with a compound (1b); (b) an activated ester method or activated amide method, that is a method by converting a carboxylic acid (8) into an activated ester for example, an activated ester of p-nitrophenyl ester, N-hydroxysuccinimide ester or 1-hydroxybenzotriazole ester; or into an activated amide for example, an activated amide of benzoxazolin-2-thion, then reacting said activated ester or activated amide with a compound (1b); (c) a carbodiimide method, that is a method by dehydrocondensing a carboxylic acid (8) with a compound (1b) in the presence of a dehydrating agent such as dicyclohexylcarbodiimide or carbonyldiimidazol; (d) a carboxylic acid halide method, that is a method by converting a carboxylic acid (8) into a corresponding carboxylic acid halide, then reacting said carboxylic acid halide with a compound (1b); (e) as to other methods, for example, a method by converting a carboxylic acid (8) into a carboxylic acid anhydride by using for example, acetic anhydride as a dehydrating agent, then reacting said carboxylic acid anhydride with a compound (1b); or a method by reacting an ester of a carboxylic acid (8) and a lower alcohol with a compound (1b) under a high pressure at an elevated temperature. Further, a method in which a carboxylic acid is activated with a phosphorus compound such triphenylphosphine or diethyl chlorophosphate, then reacting said activated carboxylic acid (8) with a compound (1b) can be applied.

As to the alkyl haloformate used in the mixed acid anhydride method, examples are methyl chloroformate, methyl bromoformate, ethyl chloroformate, ethyl-bromoformate and isobutyl chloroformate. The mixed acid anhydride is prepared by a conventional Schotten-Baumann reaction, said mixed acid anhydride is reacted, without being separated from the reaction system, with a compound (1b) to obtain indane derivative (1g) of the present invention. The Schotten-Baumann reaction is generally carried out in the presence of a basic compound. As to the basic compound, any compound usually used in Schotten-Baumann reaction can be used, and examples are organic basic compounds such as triethylamine, trimethylamine, pyridine, dimethylaniline, N-methylmorpholine, 4-dimethylaminopyridine, 1,5-diazabicyclo[4,3,0]nonene-5 (DBN), 1,8-diazabicyclo[5,4,0]undecene-7 (DBU), 1,4-diazabicyclo[2,2,2]octane (DABCO), etc.; inorganic basic compounds such as potassium carbonate, sodium carbonate, potassium hydrogencarbonate, sodium hydrogencarbonate, etc.

Said reaction is carried out at $-20°$ to $100°$ C., preferably at $0°$ to $50°$ C., and the reaction time is about 5 minutes to 10 hours, preferably 5 minutes to 2 hours. The reaction of thus obtained mixed acid anhydride with a compound (1b) is carried out at about $-20°$ to $150°$ C., preferably at about $10°$ to $50°$ C. for about 5 minutes to 10 hours, preferably for about 5 minutes to 5 hours. The mixed acid anhydride method can be carried out in the absence of a solvent, but generally is carried out in a solvent. As to the solvent used in the reaction, any solvent conventionally used in a mixed acid anhydride method can also be used, specifically, examples are halogenated hydrocarbon such as methylene chloride, chloroform, dichloroethane, etc., aromatic hydrocarbons such as benzene, toluene, xylene, etc., ethers such as diethyl ether, diisopropyl ether, tetrahydrofuran, dimethoxyethane, etc., esters such as methyl acetate, ethyl acetate, etc., aprotic polar solvents such as dimethylformamide, dimethyl sulfoxide, hexamethylphosphoryl triamide, etc.

The ratio of the amount of the carboxylic acid (8) to the amount of the alkyl haloformate and to the amount of a compound (1b) is generally at least an equimolar quantity of these reactants respectively, preferably 1 to 2 times the molar quantity of the alkyl haooformate and of a compound (1b) may be used to the carboxylic acid (8).

In carrying out the above-mentioned method of (b), i.e., an activated ester method or activated amide method, in case of using benzoxazolin-2-thionamide, the reaction is carried out in a suitable inert solvent which does not give any adverse effect to the reaction, for example a solvent similar to that of used in the above-mentioned mixed acid anhydride method or other solvent such as 1-methyl-2-pyrrolidone, at a temperature $0°$ to $150°$ C., preferably at $10°$ to $100°$ C. for 0.5 to 75 hours. The ratio of the amount of the compound (1b) to the amount of the benzoxazolin-2-thionamide is generally at least an equimolar amount, preferably an equiolar to 2 times the molar quantity of the latter is used to the former.

In the case of using N-hydroxysuccinimide ester, the reaction is advantageously carried out by using a suitable basic compound for example a basic compound which can be used in the carboxylic acid halide method as explaieed below.

The carboxylic acid halide method, i.e., method of (d), is carried out by reacting a carboxylic acid (8) with a halogenating agent to obain the corresponding carboxylic acid halide, then thus obtained carboxylic acid halide is reacted with a compound (1b), with or without separated from the reaction system and purified.

The reaction of the carboxylic acid halide with a compound (1b) is carried out in a suitable solvent in the presence of a dehydrohalogenating agent. As to the dehydrohalogenating agent, a common basic compound may be used, thus basic compounds other than those used in the above-mentioned Schotten-Baumann reaction, examples of these basic compounds are sodium hydroxide, potassium hydroxide, sodium hydride, potassium hydride, silver carbonate, alkali metal alcoholate such as sodium methylate, sodium ethylate, etc. Further, an excess amount of compound (1b) may also be used as the dehydrohalogenating agent.

As to the solvent, common solvents other than those used in the above-mentioned Schotten-Baumann reaction may be used, examples of the solvents are water, alcohols such as methanol, ethanol, propanol, butanol, 3-methoxy-1-butanol, ethyl cellosolve, methyl cellosolve, etc., pyridine, acetone, acetonitrile, etc., and a mixed solvent consisting of two or more of these solvents.

The ratio of the amount of a compound (1b) to the amount of the carboxylic acid halide is not specifically restricted and can be selected from a wide range, and generally, at least an equimolar quantity, preferably an equimolar to 2 times the molar quantity of the latter is used to the former. The reaction is generally carried out at $-30°$ to $180°$ C., preferably at about $0°$ to $150°$ C., and the reaction is generally completed in 5 minutes to 30 hours.

The carboxylic acid halide is prepared by reacting a carboxylic acid (8) with a halogenating agent in the absence or presence of a solvent. As to the solvent, any solvent which does not give any adverse effect to the reaction can be used, and examples are aromatic hydrocarbons such as benzene, toluene, xylene, etc., halogenated hydrocarbons such as chloroform, methylene chloride, carbon tetrachloride, etc., ethers such as dioxane, tetrahydrofuran, diethyl ether, etc., and aprotic polar solvents such as dimethylformamide, dimethyl sulfoxide, etc. As to the halogenating agent, a common hologentating agent which can be able to convert the hydroxyl group in the carboxyl group into the halogen atom can be used, and examples are thionyl chloride. phosphorus oxychloride, phosphorus oxybromdie, phosphorus pentachloride, phosphorus pentabromdie, etc.

The ratio of the amount of carboxylic acid (8) used to the amount of the halogentating agent is not specifically restricted and can be selected from a wide range, in the case of the reaction is carried out in the absence of a solvent, generally the latter is used in a large excess quantity to the former, while in the case of the reaction is carried out in the presence of a solvent, generally the latter is used in at lest an equimolar quantity, preferably 2 to 4 times the molar quantity to the former. The reaction temperature and the reaction time are not specifically restricted, and generally the reaction is carries out at a room temperature to $100°$ C., preferably at $50°$ to $80°$ C., for 30 minutes to 6 hours.

Above-mentioned method in which a carboxylic acid (8) is activated with a phophorus compound such as triphenylphosphine or diethyl chlorophosphate, then reacting the activated carboxylic acid (8) with a compound (1b), said reaction may be carried out in a suitable solvent. As to the solvent, any solvent which does not give any adverse effect to the reaction can be used, specifically, halogenated hydrocarbons such as methylene chloride, chloroform, dichloroethane, etc.; aromatic hydrocarbons such as benzene, toluene, xylene, etc.; ethers such as diethyl ether, tetrahydrofuran, dimethoxyethane, etc.; esters such as methyl acetate, ethyl acetate, etc.; and aprotic polar solvents such as dimethylformamide, dimethyl sulfoxide, hexamethylphosphoryl triamide, etc. can be exemplified. In this reaction, a compound (1b) per se can be able to act as a basic compound, the reaction can preferably be proceeded by using an excess amount of the compound (1b) over the theoretical quantity. If necessary, other basic compounds, for example organic basic compounds such as triethylamine, trimethylamine, pyridine, dimethylaniline, N-methylmorpholine, 4-dimethylaminopyridine, 1,5-diazabicyclo[4,3,0]nonene-5 (DBN), 1,8-diazabicyclo[5,4,0]-undecene-7 (DBU), 1,4-diazabicyclo[2,2,2]octane (DABCO), etc.; inorganic basic compounds such as potassium carbonate, sodium carbonate, potassium hydrogencarbonate, sodium hydrogencarbonate, etc. can also be used. The reaction is carried out at about 0° to 150° C., preferably at about 0° to 100° C. for about 1 to 30 hours.

The ratios of the amounts of phosphrrus compound and carboxylic acid (8) to the amount of a compound (1b) are respectively at least an equimolar quantity, preferably an equimolar quantity of 3 times the molar quantity.

Reaction scheme-6

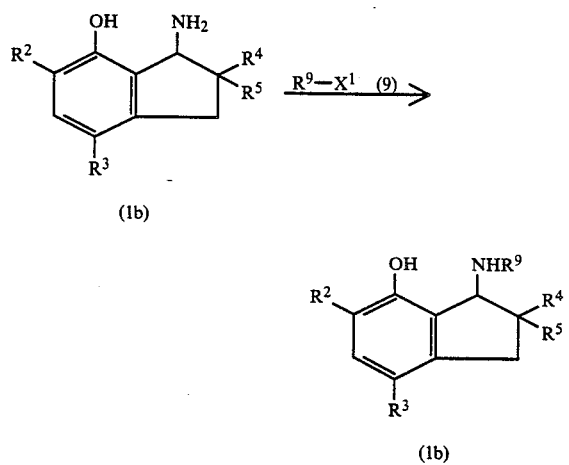

(1b)

wherein $R^2$, $R^3$, $R^4$ and $R^5$ are the same as defined above; $R^9$ is a lower alkyl group, a lower alkylsulfonyl group, a phenyl-lower alkyl group having, hydroxyl group(s) or lower alkyl group(s) as the substitutent(s) on the phenyl ring, or a phenylsulfonyl group which may have lower alkyl group(s) as the substituent(s) on the phenyl ring; $X^1$ is a halogen atom.

The reaction of a compound (1b) with a compound (9) can be carried out under conditions similar to those employed in the reaction of a compound (1b) with the carboxylic halide as in the reaction scheme-5.

In the case of a compound (1) wherein $R^1$ is an alkanoylamino group having 1 to 10 carbon atoms which may have halogen atom(s) as the substituent(s), a benzoylamino group having lower alkyl group(s) as the sbstituent(s) on the phenyl ring, or a phenyl-lower alkylamino group having a hydroxyl group(s) or a lower alkyl group(s) as the substituent(s) on the phenyl ring; $R^2$ is a lower alkanoylamino group, a lower alkanoylamino-lower alkyl group which may have halogen atom(s) as the substituent(s), a compound (1) in which $R^1$ is amino group, $R^2$ ss amino group or an amino-lower alkyl group, and $R^3$ is amino group can be obtained by hydrolysis carried out under conditions similar to those employed in the hydrolysis of a compound (2b) in reaction scheme-7 as mentioned below.

Some of compounds represented by the general formula (2) used as the starting material in the reaction scheme-1 contain novel compounds, and can be prepared by process as explained in reaction schemes-7 to -10 and -12 below.

Reaction scheme-7

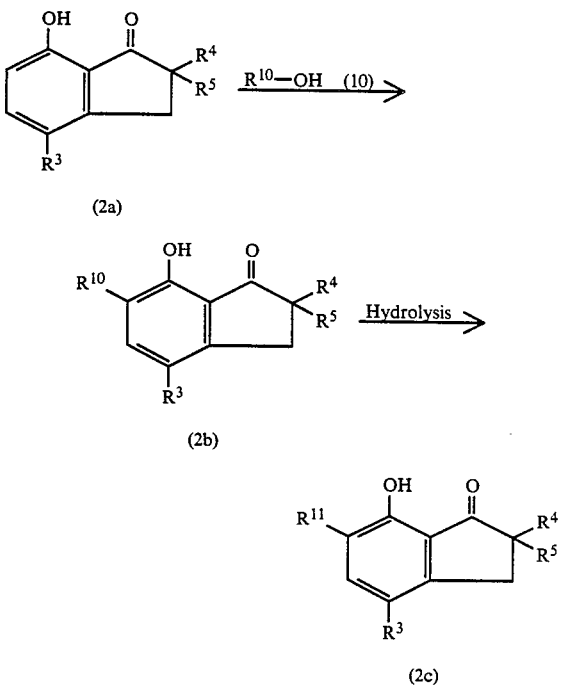

wherein $R^3$, $R^4$ and $R^5$ are the same as defined above; $R^{10}$ is a lower alkanoylamino-lower alkyl group which may have halogen atom(s) as the substituent(s); and $R^{11}$ is an amino-lower alkyl group.

The reaction of a compound (2a) with a compound (10) is carried out in the presence of a dehydrocondensing agent, in the presence or absence of a suitable solvent. As to the dehydrocondensing agent used in this reaction, examples are condensed phosphoric acids such as polyphosphoric acid, etc. phosphoric acids such as orthophosphoric acid, pyrophosphoric acid, metaphosphoric acid, etc. phosphorous acid such as orthophosphorous acid, etc.; phosphoric acid anhydride such as phosphorus pentaoxide, etc.; acids such as hydrogen chloride, sulfuric acid, boric acid, etc.; metal phosphates such as sodium phosphate, boron phosphate, ferric phosphate, aluminum phosphate, etc.; activated alumina, sodium bisulfate and Raney nickel, etc. As to the solvent used in this reaction, examples are dimethylformamide, tetrahydronaphthalene, etc.

The ratio of the amount of compound (2a) to the amount of compound (10) is not specifically restricted and can be selected from a wide range, generally an equimolar quantity or more, preferably an equimolar to 2 times the molar quantity of the latter may be used to the former. The ratio of the amount of the dehydrocondensing agent to the amount of compound (2a) is not specifically restricted and can be selected from a wide range, generally a catalytic quantity or more, preferably a large excess quantity of the dehydrocondensing agent may be used. The reaction is generally carried out at −30° to 50° C., preferably at 0° C. to about a room temperature, and is completed in 1 to 30 hours. The hydrolysis reaction of a compound (2b) may be carried out in the presence of a suitable hydrolytic catalyst for example a hydrohalic acid such as hydrochloric acid or hydrobromic acid; an inorganic acid such as sulfuric acid or phosphoric acid; an inorganic alkaline compound for example an alkali metal hydroxide such as sodium hydroxide or potassium hydroxide; an alkali metal carbonate or bicarbonate such as sodium carbonate, potassium carbonate or sodium bicarbonate, in the presence or absence of a suitable solvent for example water or a mixed solvent of water with a lower alcohol such as methanol or ethanol, and at 50° to 150° C., preferably at 70° to 100° C. for 3 to 24 hours.

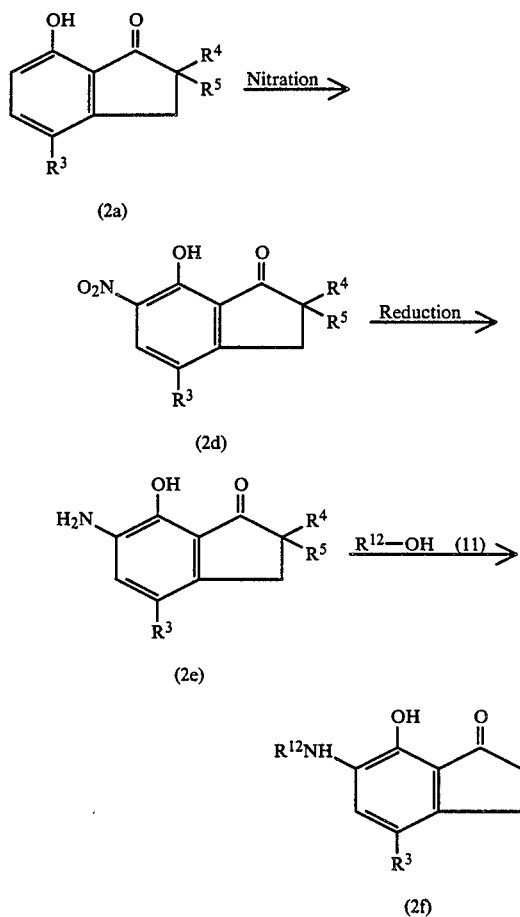

wherein $R^3$, $R^4$ and $R^5$ are the same as defined above; and $R^{12}$ a lower alkanoyl group.

The nitration reaction of a compound (2a) is generally carried out under conditions similar to those employed in a nitration of an aromatic compound, for example in the presence or absence of a suitable inert solvent, by using a nitrating agent. As to the inert solvent, examples are acetic acid, acetic anhydride, concentrated sulfuric acid, etc. As to the nitrating agent, examples are fuming nitric acid, concentrated nitric acid, a mixed acid (a mixture of sulfuric acid, a fuming sulfuric acid, phosphoric acid or acetic anhydride with nitric acid), and a mixture of sulfuric acid with an alkali metal nitrate such as potassium nitrate or sodium nitrate.

The amount of the nitrating agent used in the nitration reaction may be of an quimolar quantity or more, generally a large excess quantity. The nitration reaction is carried out advantageously at 0° C. to about a room temperature for 1 to 4 hours.

The reduction reaction of a compound (2d) can be carried out under conditions similar to those employed in the reduction reaction of a compound (1a) in the reaction scheme-1. As to the reducing agent used in the reduction reaction, examples are a mixture of iron, zinc, tin or stannous chloride with an acid usch as acetic acid, hydrochloric acid, sulfuric acid, etc., or a mixture of iron, ferrous sulfate, zinc or tin with an alkali metal hydroxide such as sodium hydroxide, a sulfide auch as ammonium sulfide, or an ammonium salt such as ammonia water, ammonium chloride. As to the inert solvent used in this reduction reaction, examples are water, acetic acid, methanol, ethanol, dioxane, etc. The reaction conditions of the above-mentioned reduction may suitably be selected according to the type of reducing agent, for example in the case of using a mixture of stannous chloride with hydrochloric acid, the reduction may be carried out advantageously at 0° C. to about a room temperature, for about 0.5 to 10 hours. The amount of the reducing agent is at least an equimolar quantity, generally an equimolar quantity to 5 times the the molar quantity thereof is used to the starting material The reaction of a compound (2e) with a compound (11) may be carried out under conditions similar to those employed in the reaction of a compound (1b) with a compound (8) in the reaction scheme-5.

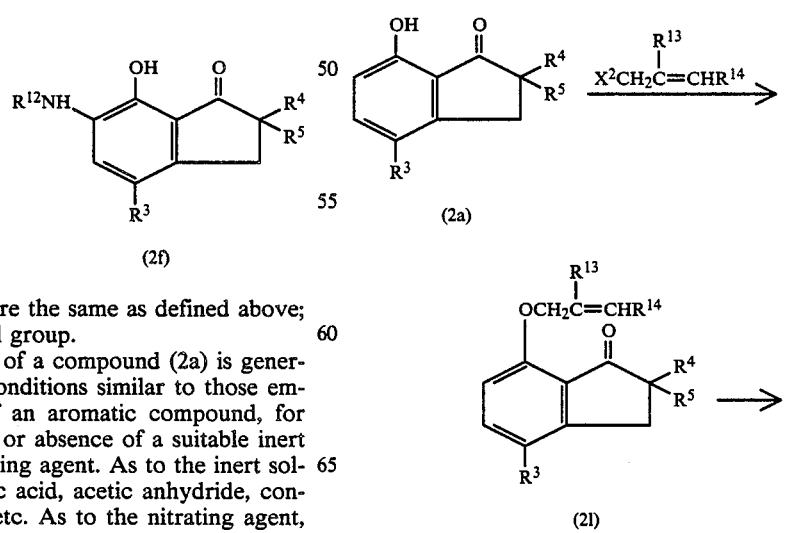

-continued

Reaction scheme-9

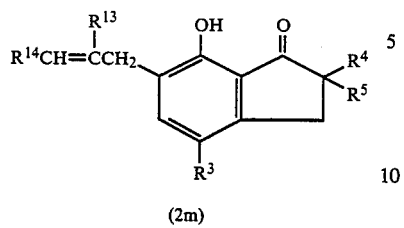

(2m)

wherein $R^3$ $R^4$ and $R^5$ are the same as defined above; $R^{13}$ and $R^{14}$ are respectively hydrogen atoms or lower alkyl group; $X^2$ is a halogen atom.

The reaction of compound (2a) with compound (12) is carried out in the presence of a basic compound. As to the basic compound used in this reaction, any basic compound widely known can be used, and examples are inorganic basic compounds such as sodium hydroxide, potassium hydroxide, sodium carbonate, potassium carbonate, sodium bicarbonate, potassium bicarbonate, silver carbonate, etc; alkali metals such as sodium and potassium, etc.; alcoholates such as sodium methylate, sodium ethylate, etc.; organic basic compound such as triethylamine, pyridine, N,N-dimethylaniline, N-methylmorpholine, 4-dimethylaminopyridine, 1,5-diazabicyclo[4,3,0]nonene-5 (DBN), 1,8-diazabicyclo[5,4,0]undecene-7 (DBU), 1,4-diazabicyclo[2,2,2]octane (DABCO), etc. The reaction can be carried out in the presence or absence of a solvent. As to the solvent used in this reaction, any inert solvent which does not give any adverse effect to the reaction can be used, and exmaples are water, alcohols such as methanol, ethanol, propanol, butanol, ethylene glycol, etc.; ethers such as dimethyl ether, tetrahydrofuran, dioxane, ethylene glycol dimethyl ther (monoglyme), diethylene glycol dimethyl ether (diglyme), etc.; ketones such acetone, methyl ethyl ketone, etc.; aromatic hydrocarbons such as benzene, toluene, xylene, etc.; esters such as methyl acetate, ethyl acetate, etc.; aprotic polar solvents such as N,N-dimethylformamide, dimethyl sulfoxide, hexamethylphosphoryl triamide, etc.; and mixed solvents thereof. The reaction can advantageously be carried out in the presence of a metal iodide such as sodium iodide or potassium iodide.

In the above-mentioned reaction of compound (2a) with compound (12), the ratio of the amount of compound (2a) to the amount of compound (12) is not specifically restricted, and can be selected from a wide range, generally, an equimolar quantity to 5 times the molar quantity, preferably an equimolar quantity to 2 times the molar quantity of the latter may be used to the fomer.

The reaction temperature is not specifically restricted, and generally the reaction is carried out at a room temperature to 200° C., preferably 50° to 150° C. The reaction tme is generally 1 to 30 hours, preferably 1 to 15 hours.

A compound (2m) can be prepared by a method so-called "Claisen Rearrangement", i.e., by heating a compound (2l) in a suitable solvent. As to the solvent used in this reaction, a solvent having high boiling point such as dimethylformamide or tetrahydronaphthalene can be exemplified. The reaction temperature is generally about 100° to 250° C., perfoerably about 150° to 250° C., and the reaction is completed in about 1 to 20 hours.

Reaction scheme-10

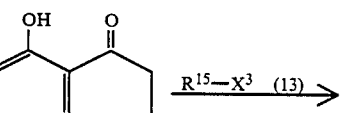

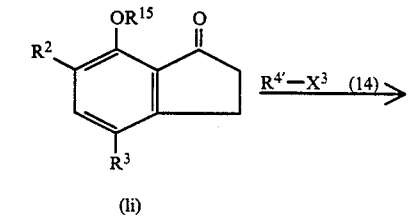

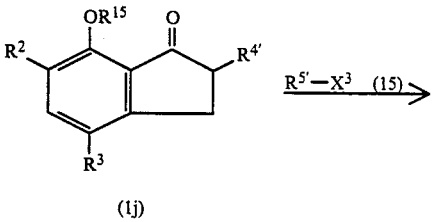

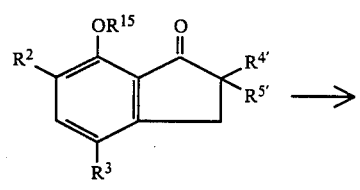

wherein $X^3$, $R^2$ and $R^3$ are the same as defined above; $R^{4'}$ and $R^{5'}$ are each a lower alkyl group; $R^{15}$ is a lower alkyl, a lower alkoxy-lower alkylene group, a lower alkanoyl group, a benzoyl group, a phenyl-lower alkyl group or a tetrahydropyranyl group.

The reaction of a compound (2i') with a compound (13) can be carried out under conditions similar to those employed in the reaction of a compound (2i) with a compound (14) as explained below.

The reaction of a compound (2i) with a compound (14) and the reaction of a compound (2j) with a compound (15) are carried out in the presence of a basic compound in a suitable solvent. As to the basic compoudd used in these reactions, examples are sodium hydroxide, potassium hydroxide, sodium ethylate, sodium hydride, potassium, sodium amide, potassium amide, etc. As to the solvent used in these reactions, examples are alcohols such as methanol, ethanol, isopropanol, etc., ethers such as dioxane, diethylene glycol dimethyl ether, etc. aromatic hydrocarbons such as toluene, xylene, etc., dimethylformamide, dimethyl sulfoxide, hexamethylphosphoryl triamide, etc.

The ratio of the amount of compound (14) or to (15) to the amount of compound (2i) or (2j) is not specifically restricted, and can be selected from a wide range, generally at least an equimolar quantity, preferably an equimolar to 5 times the molar quantity of the former may be used to the latter.

In the case of using 2 times the molar quantity more of conpound (13), the corresponding compound (2j) in which 2-position is dialkylated is predominantly obtained, and said dialkylated product can easily be separated from the monoalkylated product. The reaction is carried out generally at 0° to 70° C., preferably at 0° C. to about a room temperature, and is completed in about 0.5 to 12 hours.

A compound (2k') can be prepared from a compound (2k) in which $R^{15}$ is a phenyl-lower alkyl group, a lower alkyl group or a lower alkoxy-lower alkylene group, thus a compound (2k) is treated with a reducing catalyst such as palladium-carbon or palladium black in a suitable solvent for example water, an alcohol such as methanol, ethanol or isopropanol; an ether such as dioxane or tetrahydrofuran; or acetic acid; or a mixture of these solvents at about 0° to 100° C., under 1 to 10 atmospheric pressure of hydrogen gas for 0.5 to 3 hours; or compound (2k) is heat-treated with an acid such as hydrobromic acid or hydrochloric acid; or with an alcohol such as methanol, ethanol or isopropanol at 30° to 150° C., preferably at 50° to 120° C. Similarly, when R in the compound (2k) is a lower alkanoyl group, a tetrahydropyranyl group or a benzoyl group, the compound (2k') can be prepared by hydrolyzing said compound (2k). The hydrolysis reaction is carried out in a suitable solvent in the presence of an acid or a basic compound. As to the solvent used in this reaction, examples are water; lower alcohols such as methanol, ethanol, isopropanol, etc.; ethers such as dioxane, tetrahydrofuran, etc.; and mixtures of these solvents. As to the acid used in this reaction, examples are mineral acid such as sulfuric acid, hydrochloric acid, hydrobromic acid, etc. As to the basic compound used in this reaction, examples are metal hydroxides such as sodium hydroxide, potassium hydroxide, calcium hydroxide, etc. The hydrolysis reaction is generally carried out at a room temperature to 150° C., preferably the reaction is advantageously carried out at 80° to 120° C., and is completed in 1 to 15 hours.

Reaction scheme-11

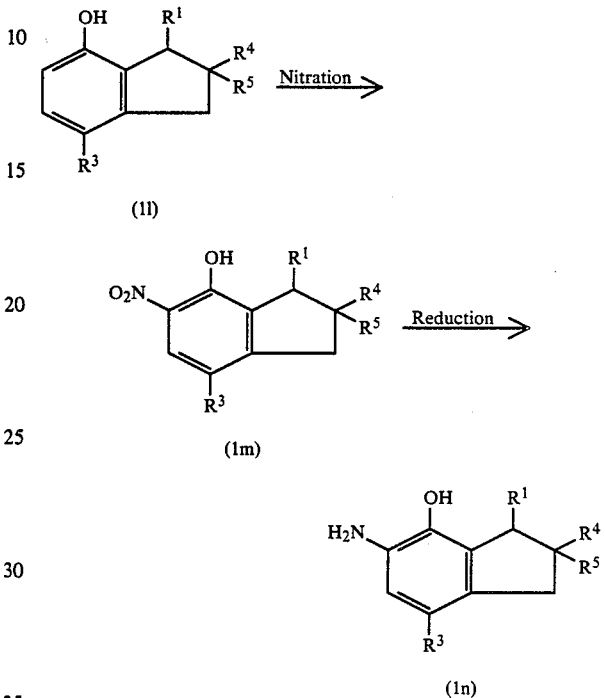

wherein $R^1$, $R^3$, $R^4$, and $R^5$ are the same as defined above.

The nitration of a compound (11) can be carried out under conditions similar to those employed in the nitration of a compound (2a) in the reaction scheme-8. The reduction fo a compound (1m) can be carried out under conditions similar to those employed in the reduction of a compound (2d) in the reaction scheme-8.

Reaction scheme-12

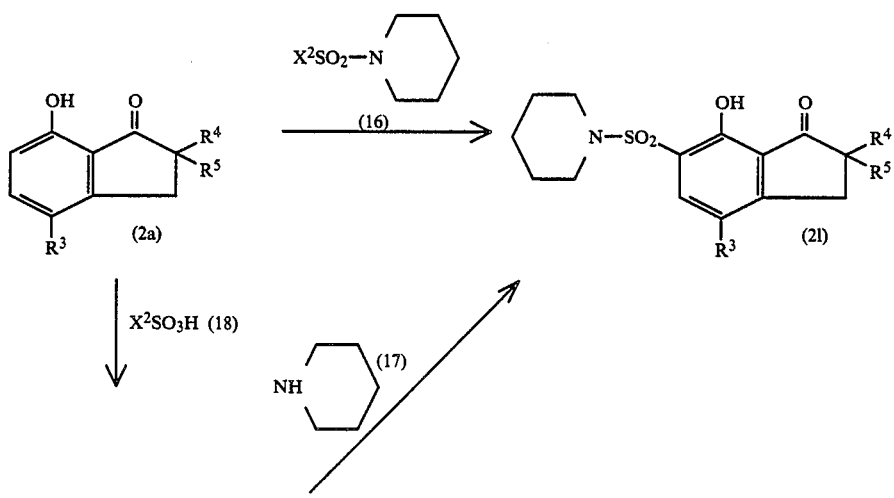

-continued
Reaction scheme-12

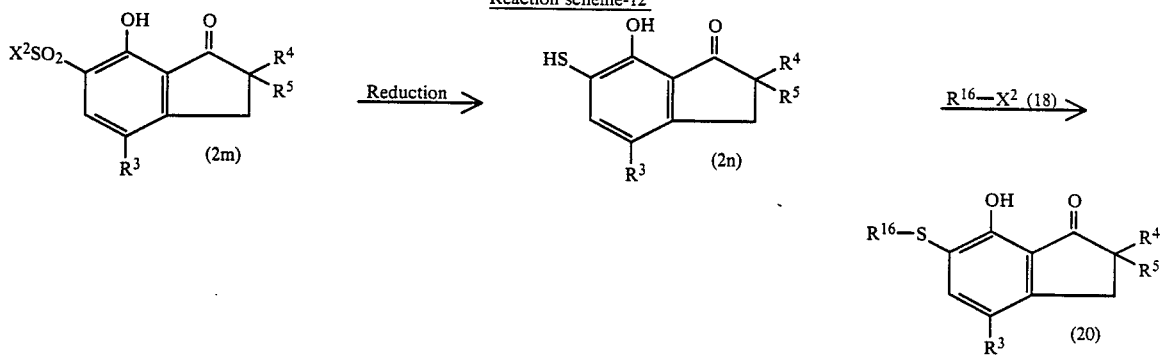

wherein $R^3$, $R^4$, $R^5$ and $X^2$ are the same as defined above; $R^{16}$ is a lower alkyl group.

The reaction of a compound (2a) with a compound (16) can be carried out in the absence or presence of a suitable solvent. As to the solvent used in this reaction, any solvent which does not give any adverse effect to the reaction may be used, exampes are halogenated hydrocarbons such as chloroform, dichloromethane, carbon tetrachloride, etc.; aromatic hydrocarbons such as benzene, toluene, xylene, etc.; nitrobenzene; dichlorobenzene, etc.

The ratio of the amount of a compound (18) to the amount of compound (2a) is at least an equimolar quantity, preferably an equimolar to 1.5 times the molar quantity of the former may be used to the latter. The reaction is generally carried out at −50° to 50° C., preferably at about −10° to 10° C., and is completed in 15 minutes to 10 hours.

The reaction of a compound (2m) with a compound (17) can be carried out in the absence or presence of a solvent, and in the presence of a dehydrohalogenating agent. As to the solvent and dehydrohalogenating agent used in this reaction, the solvent and dehydrohalogenating agent used in the reaction of a compound (1b) with a carboxylic acid halide in the reaction scheme-5 may be used.

The ratio of the amount of a dehydrohalogenating agent to the amount of a compound (2m) is at least an equimolar quantity, preferably an equimolar to 1.5 times the molar quantity of the former may be used to the latter. The ratio of the amount of piperidine of the general formula (17) to the amount of a compound (2m) is at least an equimolar, preferably an equimolar to 2 times the molar quantity of the former may be used to the latter. The reaction is generally carried out at about −30° to 150° C., preferably at bout −20° to 100° C., and is completed in about 30 minutes to 24 hours.

The reaction of a compound (2a) with a compound (16) can be carried out in the absence or presence of a solvent, and in the presence of a catalyst. As to the solvent used in this reaction, any solvent which does not give any adverse effect to the reaction may be used, and examples are chlorinated hydrocarbons such as chloroform, dichloromethane, dichloroethane, carbon tetrachloride, etc.; aromatic hydrocarbons such as benzene, toluene, xylene, nitrobenzene, dichlorobenzene; carbon disulfide, etc. As to the catalyst used in this reaction, a Lewis acid can be used, examples of the Lewis acid are aluminum chloride, zinc chloride, iron chlorides, tin chlorides, boron tribromide, boron trifluoride, a concentrated sulfuric acid, etc. The ratio of the amount of a Lewis acid to the amount of a compound (2a) may be determined optionally, and generally 2 to 6 times the molar quantity, preferably 2 to 4 times the molar quantity of the Lewis acid is used to the latter. The ratio of the amount of a compound (16) to the amount of a compound (2a) is generally at least an equimolar quantity, preferably an equimolar to 2 times the molar quantity of the former may be used to the latter. The reaction temperature is selected suitably from a wide range, and generally the reaction is carried out at about 0° to 150° C., preferably at about 0° to 100° C., and is completed in about 0.5 to 10 hours.

The reduction reaction of a compound (2m) can be carried out by a method (1) by using a combination of a metal such as iron, zinc, tin, etc., or stannous chloride with an acid such as acetic acid, hydrochloric acid, sulfuric acid, etc.; or (2) by using a hydrogeneting reducing agent such as lithium aluminum hydride, sodium borohydride, diborane, etc.

In the case of method (1), the acid is used in a large excess quantity, and the metal is used at least an equimolar quantity, generally a large eccess quantity to the amount of a compound (17). The reaction is carried out at about −50° to 150° C., preferably at a room temperature to 100° C., and is completed in about 0.5 to 10 hours. In the case of method (2), the reaction may be carried out under conditions similar to those employed in the reduction of a compound (5) in the reaction scheme-3.

The reaction of a compound (2n) with a compound (18) can be carried out in the presence of a dehydrohalogenating agent, and in the presence of a solvent. As to the solvent and dehydrohalogenating agent used in this reaction, the solvent and dehydrohalogenating agent employed in the reaction of a compound (1b) with a carboxylic acid halide in the reaction scheme-5 may be used. The reaction is generally carried out at −50° to 100° C., preferably at about −50° to 30° C., and is completed in about 30 minutes to 5 hours. The ratio of the amount of a compound (18) to the amount of a compound (2n) is at least an equimolar quantity, preferably an equimolar to 1.2 times the molar quantity may be used to the latter.

The desired indane derivatives prepared by the above-mentioned various reaction schemes can be separated and purified by usual separation means such as solvent extraction, dilution, recrystallization, column chromatography, preparative thin-layer chromatography, etc.

Indane derivatives of the present invention including inevitably their optical isomers.

Indane derivatives represented by the general formula (1) can easily be converted into their acid-addition salts by reacting with pharmaceutically acceptable acids, and the present invention also including said acid-addition salts. As to the pharmaceutically acceptable acids, examples are inorganic acids such as hydrochloric acid, hydrobromic acid, sulfuric acid, phosphoric acid, etc.; organic acid such as acetic acid, oxalic acid, succinic acid, maleic acid, fumaric acid, malic acid, tartaric acid, citric acid, malonic acid, methanesulfonic acid, benzoic acid, etc.

Among indane derivatives of the present invention, those having specific substituents are desirable, in which $R^1$ is an amino group which may have lower alkyl group(s) as the substituent(s), preferably an unsubstittted-amino group; $R^2$ is a hyhdrogen atom, a lower alkyl group, a halogen atom, a nitro group, preferably a straight chain- or branched chain-alkyl group having 2 to 6 carbon atoms, most preferably a branched chain-alkyl group having 2 to 6 carbon atoms; $R^3$ is a lower alkyl group, particularly a straight chain- or branched chain-alkyl group having 2 to 6 carbon atoms, most preferably a branched chain-alkyl group having 2 to 6 carbon atoms. As to the most desirable indane derivatives of the present invention, those having an amino group as $R^1$, and at least any one of $R^2$ or $R^3$ is an alkyl group, having 2 to 6 carbon atoms, most preferably at least any one of $R^2$ or $R^3$ is a branched chain-alkyl group having 2 to 6 carbon atoms.

Indane derivatives and salts thereof of the present invention can be used in any form of usual preparations of pharmaceutical compositions together with usual pharmaceutically acceptable carriers. Examples of pharmaceutically acceptable carriers which are selected depending on the desired form of pharmaceutical compositions including diluents and excipients such as fillers, diluents, binders, wetting agents, disintegrating agents, surface active agents, lubricants, etc. No particular restriction is made to the administration unit forms and the pharmaceutical compositions can be selected from any desired unit form including tablets, pills, powders, liquors, suspensions, emulsions, granules, capsules, supositories, injection preparations (solutions, suspensions, etc.) ointments, etc. For the purpose of to shape in the form of tablets, carriers which are widely used in this field can be used, for example excipients such as lactose, sucrose, sodium chloride, glucose, urea, starch, calcium carbonate, caolin, crystalline cellulose, silicic acid, etc.; binding agents such as water, ethanol, propanol, simple sirup, glucose solution, starch solution, gelatin solution, carboxymethyl cellulose, shelac, methyl cellulose, calcium phosphate, polyvinylpyrrolidone, etc.; desintegrating agents such as dried starch, sodium alginate, agar-agar powder, laminalia powder, sodium hydrogencarbonate, calcium carbonate, esters of polyoxyethylene sorbitan fatty acids, sodium laurylsulfate, monoglyceride of stearic acid, starch, lactose, etc.; desintegration inhibitors such as sucrose, stearin, coconut butter, hydro genated oils, etc.; absorption accelarators such as quaternary ammonium bases, sodium laurylsulfonate, etc.; wetting agents such as glycerin, starch, etc.; adsorbing agents such as starch, lactose, kaolin, bentonite, colloidal silicic acid, etc.; and lubricants such as purified talc, stearic acid salts, boric acid powder, polyethylene glycols, etc. If necessary, the tablets can further be coated with usual coating materials to make them into coated tablets, for example tablets coated with sugar, tablets coated with gelatin film, tablets coated with enteric coating layers, tablets coated with films or double layer tablets as well as multiple layer tablets, etc.

For the purpose of to shape in the form of pills, aany carrier which is known and used widely in this field can be used, for example, excipients such as glucose, lactose, starch, coconut butter, hydrogenated vegetable oils, kaolin, talc, etc.; binders such as powdered gum rrabi, powdered tragacanth gum, gelatin, ethanol, etc.; desintegrating agents such as laminaria, agar-agar, etc.

For the purpose of to shape in the form of suppositories, carriers which are known and widely used in this field can also be used, for example, polyethylene glycols, coconut butter, higher alcohols, esters of higher alcohols, gelatin, semi-synthesized glycerides, etc.

For the purpose of to make in the form of injection preparations, solutions and suspensions prepared are further sterilized and are preferably isotonic to the blood. In preparing the injection preparations in the form of solutions, emulsions, and suspensions, any carrier which is known and is widely used in this field can also be used, for example water, ethyl alcohol, propylene glycol, ethoxylaeed isostearyl alcohol, polyoxylated isostearyl alcohol, polyoxyethylene sorbitan fatty acid esters, etc. In these instances, adequate amounts of sodium chloride, glucose or glycerin may be added to the desired injection preparations to make them isotonic. Furthermore, usual dissolving agents, buffer solutions, analgesic agents may be added. Also coloring materials, preservitives, perfumes, seasoning agents, sweetening agents and other medicines may be added in the desired pharmaceutical preparations, if necessary.

For the purpose of to make the preparations in the form of pastes, creams and gels, diluents which are known and widely used in this field can also be used, for eexamples white petrolatum, paraffin, glycerin, cellulose derivatives, polyethylene glycols, silicones, bentonite, etc.

The amount of indane derivative of the present invention represented by the general formula (1) or their acid addition salt to be contained in pharmaceutical composition is not specifically restricted, and can suitably be selected from a wide range, generally 1 to 70% by weight of the indane derivative or its acid salt is contained in the composition.

Methods for administrating the above-mentioned pharmaceutical compositions are not specifically restricted, the compositions can be used in various forms of preparations depending upon the age, the distinction of sex, the degree of symptoms and other conditions of the patient without any restriction. For example, tablets, pills, solutions, suspensions, emulsions, granules and capsules are administered orally; injection preparations are administered intraveneously singly, or administered with usual injectable transfusions such as glucose solutions, amino acids solutions, etc.; if necessary, the injection preparations are administered singly intramuscularly, intracutaneously, subcutaneously or intraperitoneally; and the suppositories are administered into rectum.

The dosage of the above-mentioned pharmaceutical preparations can be selected suitably according to the methods for administrations, the age of the patient, the distinction of sex and other conditions as well as the degree of the symptoms, and generally pharmaceutical compositions containing 0.2 to 200 mg per kg of the body weight per day of the indane derivative or its acid addition salt represented by the general formula (1) may be used.

REFERENCE EXAMPLE 1

9.3 Grams of 4-methyl-7-hydroxy-1-indanone and 30 g of N-hydroxymethyl-α-chloroacetamide were dissolved by adding 280 ml of concentrated sulfuric acid under a cooling condition. After the mixture was allowed to stand overnight, the mixture was poured into ice-water. The crystals formed in the mixture were collected by filtration and were recrystallized from ethanol to obtain 49 g of 4-methyl-6-α-chloroacetylaminomethyl-7-hydroxy-1-indanone.
Colorless needle-like crystals
Melting point: 166°–167.5° C.

REFERENCE EXAMPLE 2

Into a solution of 25.6 g of 4-methyl-7-hydroxy-1-indanone in 250 ml of acetic acid was added 19.4 ml of acetic anhydride and a solution of 15.4 ml of concentrated nitric acid in 50 ml of acetic acid gradually. The reaction mixture was concentrated to drynsss, and the residue was washed with ether to obtain 25.7 g of 4-methyl-6-nitro-7-hydroxy-1-indanone.
Yellow needle-like crystals
Melting point: 154°–157° C.

REFERENCE EXAMPLE 3

Into a solution of 26.0 g of 4-methyl-6-nitro-7-hydroxy-1-indanone in 50 ml of dimethylformamide was added 2.6 g of 10% palladium carbon, then the mixture was subjected to a catalytic hydrogenation under an atmospheric pressure at 0° C. to a room temperature. The catalyst was removed by filtration and the solvent was removed by evaporation to obtain 17.3 g of 6-amino-4-methyl-7-hydroxy-1-indanone.
Pale yellow needle-like crystals
Melting point: 187°–188° C. (decomp.)

REFERENCE EXAMPLE 4

3 Grams of 4-methyl-6-α-chloroacetylaminomethyl-7-hydroxy-1-indanone and a solution of 30 ml of concentrated sulfuric acid in 60 ml of ethanol were refluxed by heating for 8 hours. The solvent was removed by evaporation, the residue thus obtained was recrystallized from ethanol to obtain 1 g of 4-methyl-6-aminomethyl-7-hydroxy-1-indanone.
Pale yellow flake-like crystals
Melting point: Over 300° C.
NMR (DMSO)67 : 2.22 (s. 3H), 2.6–2.8 (m. 2H), 2.85–3.1 (m. 2H), 3.97 (s. 2H),
7.55 (s. 1H), 8.4–9.5 (br. 3H)

REFERENCE EXAMPLE 5

Into a solution of 11.5 g of 4-methyl-6-nitro-7-hydroxy-1-indanone in 500 ml of acetic acid was added 1.5 g of 5% palladium carbon, then the mixture was subjected to a catalytic hydrogenation under an atmospheric pressure at a room temperature. The catalyst was removed by filtration and the solvent was removed by evaporation. The residue obtained was washed with ether and was recrystallized from methanol to obtain 6.34 g of 4-methyl-6-acetamido-7-hydroxy-1-indanone.
Reddish orange needle-like crystals
Melting point: 193°–198° C.
NMR (DMSO)δ: 2.1 (s. 3H), 2.17 (s. 3H), 2.45–2.77 (m. 2H), 2.77–3.1 (m. 2H), 7.67 (s. 1H), 9.25–10 (br. 2H).

REFERENCE EXAMPLE 6

Into a solution of 36 g of 4-methyl-7-hydroxy-1-indanone and 17.6 g of potassium hydroxide in 650 ml of methanol was added 25 ml of allyl bromide, and the mixture was refluxed by heating for 6 hours. The insoluble matters in the reaction mixture were removed by filtration, then the solvent was removed by evaporation. The residue obtained was extracted with chloroform-water, and the chloroform layer was collected by separation, then the solvent was removed by evaporation. The residue thus obtained was washed with ether and purified by means of a column chromatography to obtain 32 g of 4-methyl-7-allyloxy-1-indanone.
Pale yellow powdery crystals
Melting point: 89°–92° C.

REFERENCE EXAMPLE 7

32 Grams of 4-methyl-7-allyloxy-1-indanone was suspended in 100 ml of tetrahydronaphthalene. The suspension was refluxed by heating for 4 hours under argon gas atmosphere. The reaction mixture was subjected to a silica gel column chromatography (eluent: n-hexane, and dichloromethane: n-hexane=1:2) to obtain 26.8 g of 4-methyl-6-allyl-7-hydroxy-1-indanone.
Pale brown needle-like crystals
Melting point: 41°–45° C.

REFERENCE EXAMPLE 8

Into a solution of 10 g of 4-methyl-7-hydroxy-1-indanone and 5.3 g of potassium hydroxide in 200 ml of methanol was added 8.2 ml of crotyl bromide, and the mixture was refluxed by heating for 4 hours. The insoluble matters in the reaction mixture were removed by filtration, then the solvent was removed by evaporation. The residue obtained was extracted with chloroform-water, and the chloroform layer was washed with a diluted sodium hydroxide aqueous solution, then washed with water, dried with anhydrous magnesium sulfate, and the solvent was removed by evaporation. The residue obtained was purified by means of a silica gel column chromatography (eluent: n-hexane: dichloromethane=1:1) to obtain 8.72 g of 4-methyl-7-crotyloxy-1-indanone.
Pale yellow needle-like crystals
Melting point: 87.5°–92° C.

REFERENCE EXAMPLE 9

8 Grams of 4-methyl-7-crotyloxy-1-indanone was suspended in 50 ml of tetrahydronaphthalene. The suspension was refluxed by heating for 9 hours under argon gas atmosphere. The reaction mixture was purified by means of a silica gel column chromatography (eluent: n-hexane, then a mixture of n-hexane: dichloromethane=2:1) and was recrystallized from a mixture of dichloromethane with n-hexane to obtain 5.44 g of 4-methyl-6-(1-methyl-2-propenyl)-1-indanone.
Colorless needle-like crystals
Melting point: 88°–92° C.

REFERENCE EXAMPLE 10

Into a solution of 15 g of 4-methyl-7-hydroxy-1-indanone and 7.95 g of potassium hydroxide in 200 ml of methanol was added 13.55 ml of methallyl chloride, and the mixture was refluxed by heating for 11 hours. The insoluble matters in the reaction mixture were removed by filtration, then the solvent was removed by evaporation. The residue obtained was purified by means of a silica gel column chromatography (eluent: n-hexane: dichloromethane=1:1) to obtain 9 g of 4-methyl-7-methallyloxy-1-indanone.

Colorless powdery crystals
Melting point: 74.2°-75.2° C.

REFERENCE EXAMPLE 11

8.46 Grams of 4-methyl-7-methallyoxyl-1-indanone was added in 50 ml of tetrahydronaphthalene, and the mixture was refluxed by heating for 9 hours. The reaction mixture was treated by means of a silica gel column chromatography (eleent: n-hexane: dichloromethane=2:1) and the product was recrystallized from dichloromethane-n-hexane to obtain 6.68 g of 4-methyl-6-(2-methyl-2-propenyl)-7-hydroxy-1-indanone.

Colorless needle-like crystals
Melting point: 62.5°-64° C.

REFERENCE EXAMPLES 12 to 14

By a method similar to those described in Reference Examples 8 and 9, the following compounds were prepared as shown in Table 1.

TABLE 1

| Reference Example | R² | R³ | R⁴ | R⁵ | Melting point (°C.) (Recrystalization solvent) | Crystal form |
|---|---|---|---|---|---|---|
| 12 | —CH₂CH=CH₂ | H | H | H | | Oily substance |
| 13 | —CH₂CH=CH₂ | C₂H₅ | H | H | | Oily substance |
| 14 | CH₃<br>\|<br>—CHCH=CH₂ | C₂H₅ | H | H | 67–68.5 (Petroleum ether) | Colorless needle-like crystals |

REFERENCE EXAMPLE 15

Into a solution of 90 ml of chlorosulfonic acid in 150 ml of carbon tetrachloride was added 30 g of 7-hydroxy-4-methyl-1-indanone gradually under an ice-cooling condition. The carbon tetrachloride layer was removed by separation, and one liter of ice-water was added into the residual layer then the mixture was stirred vigorously. The solid matter precipitated was collected by filtration, then washed with water to obtain 8.7 g of 7-hydroxy-6-chlorosulfonyl-4-methyl-1-indanone. This product was added, without purified, to a solution consisting of 31.4 g of stannous chloride dihydrate and 100 ml of concentrated hydrochloric acid, and the mixture was stirred at a room temperature for 4 hours. The reaction mixture was poured into 500 ml of ice-water, the crystals precipitated were collected by filtration, washed with water, dried to obtain 7.86 g of 7-hydroxy-6-mercapto-4-methyl-1-indanone. Next, this product was suspended, without purified, in 100 ml of methanol, then to this suspension was added 3.9 ml of methyl iodide and a solution of 5.1 g of sodium bicarbonate in 20 ml of water, the whole mixture was stirred at a room temperature for 1 hour. The mixture was concentrated under a reduced pressure to remove the solvent to dryness. The residue was purified by means of a silica gel column chromatography (eluent: chloroform) and recrystallized from ethanol to obtain 1.52 g of 7-hydroxy-4-methyl-6-methylthio-1-indanone.

Colorless needle-like crystals
Melting point: 139° C.

REFERENCE EXAMPLE 16

Into a solution of 2 g of 7-hydroxy-4-methyl-1-indanone in 10 ml of dichloroethane was added 2.27 g of 1-piperidine sulfonyl chloride. Then 10 g of anhydrous aluminum chloride was gradually added to the mixture and stirred, and the reaction mixture was refluxed by heating for 8 hours. The reaction mixture was extracted with 200 ml of chloroform, washed with water, then the chloroform was removed by evaporation under a reduced pressure. The residue was purified by means of a silica gel column chromatography (eluent: chloroform), and recrystallized from ethanol to obtain 1.24 g of 7-hydroxy-4-methyl-6-(1-piperidinesulfonyl)-1-indanone.

Pale yellow plate-like crystals
Melting point: 188°-189° C.

REFERENCE EXAMPLE 17

Into a solution of 7.56 g of 4,6-dimethyl-7-methoxymethyleneoxy-1-indanone in 200 ml dimethylformamide was added 4.94 g of 60% sodium hydride gradually at a room temperature and the reaction mixture was stirred for about 1 hour until the generation of hydrogen gas ceased. Then 14.6 g of methyl iodide was added to the reaction mixture and was stirred at a room temperature for 2 hours. The reaction mixture was acidified by adding hydrochloric acid, then the solvent was removed by evaporation under a reduced pressure. The residue obtained waspoured into 1 liter of water under vigorous agitation, and extracted with 300 ml of ethyl acetate twice, the extract was washed with water, and dried with anhydrous magnesium sulfate. The solvent was removed by evaporation under a reduced pressure to obtain 8 g of 7-methoxymethyleneoxy-2,2,4,6-tetramethyl-1-indanone. This product was, without purified, dissolved in 200 ml of methanol, and 10 ml of concentrated hydrochloric acid was added to this solution, then stirred at 50° C. for 3 hours, and methanol was removed by evaporation under a reduced pressure. The residue was purified by means of a silica gel column chromatography (eluent: n-hexane: dichloromethane=2:1) to obtain 6.8 g of 7-hydroxy-2,2,4,6-tetramethyl-1-indanone.

Melting point: 28°-30° C.

NMR (CDCl₃)δ: 9.08 (1H, s.), 7.19 (1H, s.), 2.84 (2H, s.), 2.23 (3H, s.), 2.20 (3H, s.), 1.28 (6H, s.)

EXAMPLE 1

28 Grams of hydroxylamine hydrochloride and 56 g of potassium carbonate were added in 400 ml of methanol, and the mixture was refluxed by hetting for 30 minutes. After cooling the reaction mixture to a room temperature, the supernatant liquor was collected by separation to prepare a methanol solution of hydroxylamine. To this methanol solution of hydroxylamine was added 16.2 g of 7-hydroxy-4-methyl-1-indanone and refluxed by heating for 5 hours under stirring condition. The reaction mixture was concentrated to dryness under a reduced pressure. To the residue thus obtained was added 200 ml of ethyl acetate, then the insoluble matter was removed by filtration. The filtrate was concentrated to dryness under a reduced pressure, and the residue was recrystallized from methanol to obtain 17.6 g of 7-hydroxy-4-methyl-1-indanone oxime in the form of colorless needle-like crystals.

Melting point: 148°–149.5° C.

EXAMPLES 2–12

By a method similar to that described in Example 1 and using a suitable starting material, there were prepared compounds of Examples 2–12 as shown in Table 2 as follows.

platinum oxide catalyst was added thereto and the mixture was subjected to catalytic reduction under 5 atmospheric pressure of hydrogen gas at a room temperature for 8 hours. The catalyst was removed by filtration, then the filtrate was concentrated to dryness under a reduced pressure. The residue thus obtained was dissolved in 200 ml of ethanol and hydrogen chloride gas was blown into the solution to become saturated. The solvent was removed by evaporation under a reduced pressure, the residue was recrystallized from ethanol to obtain 3.30 g of 1-amino-7-hydroxy-4-methylindane hydrochloride in the form of colorless needle-like crystals. Melting point: 221°–223° C.

EXAMPLES 14–29

TABLE 2

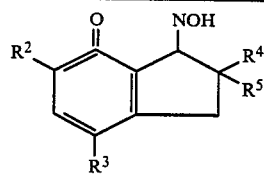

| Example No. | $R^2$ | $R^3$ | $R^4$ | $R^5$ | Melting point (°C.) (Recrystallization solvent) | Crystal form |
|---|---|---|---|---|---|---|
| 2 | —CH$_2$NHCOCH$_2$Cl | CH$_3$ | H | H | 194.7–197 (Ethanol) | Colorless needle-like crystals |
| 3 | —NHCOCH$_3$ | CH$_3$ | H | H | 192.5–196 (Methanol) | Colorless needle-like crystals |
| 4 | —CH$_2$CH=CH$_2$ | CH$_3$ | H | H | 96.5–98.5 (n-Hexane) | Pale yellow flake-like crystals |
| 5 | —CHCH=CH$_2$<br>\|<br>CH$_3$ | CH$_3$ | H | H | 161.5–164 (n-Hexane-ether) | Colorless powdery substance |
| 6 | —CH$_2$C=CH$_2$<br>\|<br>CH$_3$ | CH$_3$ | H | H | 132–133.5 (n-Hexane-ether) | Yellow powdery substance |
| 7 | —NH$_2$ | CH$_3$ | H | H | 215–217 (Decomposed) (Ethanol) | Colorless needle- |
| 8 | —CH$_3$ | CH$_3$ | H | H | 155–156 (Methanol) | Colorless needle-like crystals |
| 9 | —CH$_2$CH=CH$_2$ | H | H | H | 104–104.5 (Hexane) | Colorless needle-like crystals |
| 10 | —CH$_2$CH=CH$_2$ | C$_2$H$_5$ | H | H | 91.5–92.0 (Hexane) | Colorless flake-like crystals |
| 11 | —CH$_3$ | CH$_3$ | CH$_3$ | CH$_3$ | 156–157 (Ethanol-diethyl ether) | Colorless needle-like crystals |
| 12 | —CHCH=CH$_2$<br>\|<br>CH$_3$ | C$_2$H$_5$ | H | H | 153.5–154.5 (Ethyl acetate-n-hexane) | Pale yellow flake-like crystals |

EXAMPLE 13

15.0 Grams of 7-hydroxy-4-methyl-1-indanone oxime was dissolved in 200 ml of acetic acid, then 1.0 g of By a method similar to that described in Example 13, and using a suitable starting material, there were prepared compounds of Examples 14–29 as shown in Table 3 as follows.

TABLE 3

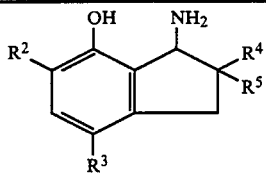

| Example No. | $R^2$ | $R^3$ | $R^4$ | $R^5$ | Melting point (°C.) (Recrystallization solvent) | Crystal form | Salt |
|---|---|---|---|---|---|---|---|
| 14 | —CH₃ | CH₃ | H | H | 229–230 (decomp.) (Isopropanol) | Colorless needle-like crystals | HCl |
| 15 | —H | H | H | H | 200–202 (Methanol) | Colorless needle-like crystals | HCl |
| 16 | —I | CH₃ | H | H | Over 200 (decomp.) | Yellow needle-like crystals | HCl |
| 17 | —Cl | Cl | H | H | 238–239 (decomp.) | Colorless prism-like crystals | HCl |
| 18 | —Br | CH₃ | H | H | 178–190 (decomp.) (Isopropanol) | Colorless needle-like crystals | HBr |
| 19 | —CH₂NHCOCH₂Cl | CH₃ | H | H | 204 (Ethanol-ether) | Colorless needle-like crystals | HCl |
| 20 | —NH₂ | CH₃ | H | H | 204 (decomp.) (Ethanol) | Colorless powdery substance | 2HCl |
| 21 | —CH₂NH₂ | CH₃ | H | H | 220 (decomp.) | Colorless powdery substance | 2HCl |
| 22 | —NHCOCH₃ | CH₃ | H | H | 205–215 (decomp.) (Methanol) | Colorless powdery substance | HCl |
| 23 | —C₃H₇ | CH₃ | H | H | 174–175.5 (Ethanol-ether) | Colorless powdery substance | HCl |
| 24 | —CH—C₂H₅<br>\|<br>CH₃ | CH₃ | H | H | 177.5–179 (Methanol-ether) | Colorless powdery substance | HCl |
| 25 | —CH₂CH—CH₃<br>\|<br>CH₃ | CH₃ | H | H | 186–187 (Methanol-ether) | Colorless powdery substance | HCl |
| 26 | —C₃H₇ | H | H | H | 175–176 (Ethanol-ether) | Colorless powdery substance | HCl |
| 27 | —C₃H₇ | C₂H₅ | H | H | 156–158 (Ethanol-ether) | Colorless powdery substance | HCl |
| 28 | —CH₃ | CH₃ | CH₃ | CH₃ | 231–233 (Ethyl acetate) | Colorless needle-like crystals | HCl |
| 29 | —CH—C₂H₅<br>\|<br>CH₃ | C₂H₅ | H | H | 194–195 (decomp.) (Ethanol-ether) | Colorless powdery substance | HCl |

EXAMPLE 30

One gram of 1-amino-7-hydroxy-4-methylindane hydrochloride was dissolved in 20 ml of water, then 5 ml of 3N-hydrochloric acid solution containing 0.85 g of iodine monochloride was added dropwise at a room temperature under vigorous stirring condition. The reaction mixture was stirred at the same temperature for 2 hours, then ice-cooled. The crystals precipitated were collected by filtration, and changed them to hydrochloride, washed with ether and dried. 0.70 Grams of 1-amino-7-hydroxy-6-iodo-4-methylindane hydrochloride was obtained in the form of yellow needle-like crystals. Melting point: Over 200° C. (decomp.).

EXAMPLE 31

1.0 Gram of 1-mmino-7-hydroxyindane hydrochloride was dissolved in 60 ml of acetic acid, then 1.53 g of sulfuryl chloride was added dropwise under ice-cooling condition. The reaction mixture was stirred at the same temperature for 3 hours, concentrated under a reduced pressure. The residue was dissolved in 50 ml of ethanol being saturated with hydrogen chloride gas, and dried under a reduced pressure. Recrystallized from isopropanolether to obtain 0.43 g of 1-amino-4,6-dichloro- 7-hydroxyindane hydrochloride in the form of colorless prism-like crystals. Melting point: 238°–239° C. (decomp.).

EXAMPLE 32

5 Grams of 1-amino-7-hydroxy-4-methylindane was dissolved in 30 ml of acetic acid, then an acetic acid solution containing 1.73 ml of bromine was added and stirred at a room temperature for 1 hour. The crystals precipitated were collected by filtration, and were recrystallized from isopropanol to obtain 2 g of 1-amino-6-bromo-7-hydroxy-4-methylindane hydrobromide in the form of yellow needle-like crystals. Melting point: 178°–190° C. (decomp.) The structure was determined by means of NMR.

NMR (DMSO)δ: 2.18 (s. 3H), 1.8–3.35 (m. 4H), 4.75–5.05 (m. 1H), 7.35 (s. 1H), 7.6–9.2 (b. s., 3H).

EXAMPLE 33

5.75 Grams of 1-amino-7-hydroxy-4-methylindane hydrochloride was suspended in 40 ml of acetic acid, then 3.27 ml of acetic anhydride and a solution consisting of 2.59 ml of concentrated nitric acid and 10 ml of acetic acid were added thereto, and the whole mixture was stirred at a room temperature for 6 hours. The solvent was removed by evaporation, the residue was washed with acetone and recrystallized from ethanol to obtain 2 g of 1-amino-7-hydroxy-4-methyl-6-nitroindane hydrochloride in the form of yellow needle-like crystals. Melting point: 200°–230° C. (decomp.).

NMR (DMSO)δ: 2.22 (s. 3H), 2.0–3.45 (m. 4H), 4.7–5.0 (m. 1H), 7.82 (s. 1H), 8.4–9.7 (br. 3H).

EXAMPLE 34

1.77 Grams of 1-amino-4,6-dimethyl-7-hydroxyindane was dissolved in 100 ml of 0.2N-sodium hdyroxide aqueous solution, then 1.7 g of α-chloroacetyl chloride was added thereto under an ice-cooling condition. Then the reaction mixture was stirred at a room temperature for 2 hours. The reaction mixture was acidified by adding a diluted hydrochloric acid, then extracted with chloroform. The chloroform layer was washed with water, dried, then the solvent was removed by evaporation. Recrystallized from ethanol to obtain 2.34 g of 1-acetylamino-4,6-dimethyl-7-hydroxyindane in the form of colorless needle-like crystals. Melting point: 131°–132° C.

EXAMPLES 35-37

By a method smmilar to that described in Example 34, by using a suitable starting materials, there were prepared compounds of Examples 55-37 as shown in Table 4 as follows.

TABLE 4

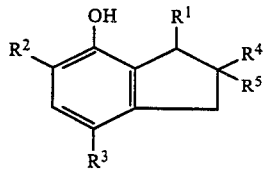

| Example No. | $R^1$ | $R^2$ | $R^3$ | $R^4$ | $R^5$ | Melting point (°C.) (Recrystallization solvent) | Crystal form |
| --- | --- | --- | --- | --- | --- | --- | --- |
| 35 | —NHCO(CH$_2$)$_8$CH$_3$ | CH$_3$ | CH$_3$ | H | H | 103–104 (n-Hexane) | Colorless needle-like crystals |
| 36 | —NHCO—⟨⟩—CH$_3$ | CH$_3$ | CH$_3$ | H | H | 230–232 (Ether-n-hexane) | Colorless needle-like crystals |
| 37 | —NHCOCH$_2$Cl | CH$_3$ | CH$_3$ | H | H | 131–132 (Ethanol) | Colorless needle-like crystals |

EXAMPLE 38

Into 100 ml of a chloroform solution containing 1.77 g of 1-amino-4,6-dimethyl-7-hydroxyindane and 2 ml of triethylamine was added dropwise 1.72 g of methanesulfonyl chloride at a room temperature, the mixture was stirred at the same temperature for 4 hours. The reaction mixture was washed with a diluted hydrochloric acid, water, a saturated sodium bicarbonate aqueous solution, water and a saturated sodium chloride aqueous solution, in this order, then dried with anhydrous sodium sulfate. The solvent was removed by evaporation and the residue was recrystallized from ether-n-hexane to obtain 0.58 g of 1-methanesulfonylamino-4,6-dimethyl-7-hydroxyindane in the form of colorless powdery substance. Melting point: 114°–116° C.

EXAMPLES 39-47

By a method similar to that described in Example 38, by using a suitable starting material, there were prepared compounds of Examples 39–47 as shown in Table 5 as follows.

TABLE 5

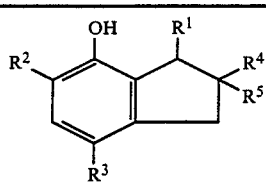

| Example No. | $R^1$ | $R^2$ | $R^3$ | $R^4$ | $R^5$ | Melting point (°C.) (Recrystallization solvent) | Crystal form | Salt |
|---|---|---|---|---|---|---|---|---|
| 39 | —NHSO$_2$—C$_6$H$_4$—CH$_3$ | CH$_3$ | CH$_3$ | H | H | 143–145 (Ether-n-hexane) | Colorless needle-like crystals | — |
| 40 | —NH—n-C$_4$H$_9$ | CH$_3$ | CH$_3$ | H | H | 143–144 (Ethanol-ether) | Colorless powdery substance | HCl |
| 41 | —NHCH$_2$(CH$_2$)$_4$CH$_3$ | CH$_3$ | CH$_3$ | H | H | 146–148 (Ether) | Colorless needle-like crystals | HCl |
| 42 | —NHCH$_2$—[2,6-di-t-C$_4$H$_9$-4-OH-phenyl] | CH$_3$ | CH$_3$ | H | H | 154–155 (Ether-n-hexane) | Colorless needle-like crystals | — |
| 43 | —NHCH$_3$ | CH$_3$ | CH$_3$ | H | H | 221–223 (Ethanol-ether) | Colorless needle-like crystals | HCl |
| 44 | —NHCH$_3$ | —SCH$_3$ | CH$_3$ | H | H | 172.5–173.5 (Ether-ethanol) | Colorless powdery substance | HCl |
| 45 | —NHCH$_3$ | —SO$_2$—N(piperidine) | CH$_3$ | H | H | 161–162 (Ether-n-hexane) | Pale brown powdery substance | — |
| 46 | —NHCH$_3$ | —CH$_2$CH=CH$_2$ | C$_2$H$_5$ | H | H | 172–173 (decomp.) (Ethanol-ether) | Colorless flake-like crystals | HCl |
| 47 | —NHCH$_3$ | —CH(CH$_3$)—CH=CH$_3$ | C$_2$H$_5$ | H | H | 169–170 (decomp.) (Ethanol-ether) | Colorless flake-like crystals | HCl |
| 48 | —NHCH$_3$ | —C$_2$H$_5$ | CH$_3$ | H | H | 175.5–176.5 (Ethanol-ether) | Colorless flake-like crystals | HCl |
| 49 | —NHCH$_3$ | —CH$_3$ | C$_2$H$_5$ | H | H | 217–218 (Ethanol) | Colorless powdery substance | HCl |

EXAMPLE 50

100 Milliliters of ethanol solution containing 1.76 g of 4,6-dimethyl-7-hydroxy-1-indanone and 14.6 g of n-butylamine was refluxed by heating for 8 hours. The reaction mixture was cooled to a room temperature, then 1.0 g of sodium borohydride was added thereto. The mixture was further stirred at a room temperature for 1 hour. The reaction mixture was concentrated to dryness and the residue obtained was dissolved in 100 ml of water. Then the solution was acidified by adding a concentrated hydrochloric acid, and the pH of the solution was adjusted to about pH=9 by adding a saturated sodium acetate aqueous solution. The precipitate formed was extracted with ethyl acetate, washed with water and dried. The solvent was removed by evaporation, the residue obtained was dissolved in 100 ml of ethanol, and changed to hydrochloride by adding ethanol being saturated with hydrogen chloride gas. Recrystallized from ethanol-ether to obtain 1.89 g of 1-n-butylamino-4,6-dimethyl-7-hydroxyindane hydrochloride in the form of colorless needle-liee crystals. Melting point: 143°–144° C.

EXAMPLES 51-61

By a method siiilar to that described in Example 50, by using a suitable starting material, there were prepared compounds of Example 51-61 as shown in Table 6 as follows.

TABLE 6

Structure:

$R^2$ and OH on benzene ring fused to cyclopentane ring bearing $R^1$, $R^4$, $R^5$; $R^3$ on benzene ring.

| Example No. | $R^1$ | $R^2$ | $R^3$ | $R^4$ | $R^5$ | Melting point (°C.) (Recrystalization solvent) | Crystal form | Salt |
|---|---|---|---|---|---|---|---|---|
| 51 | —NHCH$_2$(CH$_2$)$_4$CH$_3$ | CH$_3$ | CH$_3$ | H | H | 146–148 (Ether) | Colorless needle-like crystals | HCl |
| 52 | —NHCH$_2$—(3,5-di-t-C$_4$H$_9$-4-OH-phenyl) | CH$_3$ | CH$_3$ | H | H | 154–155 (Ether-n-hexane) | Colorless needle-like crystals | — |
| 53 | —NHCH$_3$ | CH$_3$ | CH$_3$ | H | H | 221–223 (Ethanol-ether) | Colorless needle-like crystals | HCl |
| 54 | —NHSO$_2$CH$_3$ | CH$_3$ | CH$_3$ | H | H | 114–116 (Ether-n-hexane) | Colorless powdery substance | — |
| 55 | —NHSO$_2$—(4-CH$_3$-phenyl) | CH$_3$ | CH$_3$ | H | H | 143–145 (Ether-n-hexane) | Colorless needle-like crystals | — |
| 56 | —NHCH$_3$ | —SCH$_3$ | CH$_3$ | H | H | 172.5–173.5 (Ether-ethanol) | Colorless powdery substance | HCl |
| 57 | —NHCH$_3$ | —SO$_2$—N(piperidino) | CH$_3$ | H | H | 161–162 (Ether-n-hexane) | Pale brown powdery substance | — |
| 58 | —NHCH$_3$ | —CH$_3$ | C$_2$H$_5$ | H | H | 217–218 (Ethanol) | Colorless powdery substance | HCl |
| 59 | —NHCH$_3$ | —CH$_2$CH=CH$_2$ | C$_2$H$_5$ | H | H | 172–173 (decomp.) (Ethanol-ether) | Colorless flake-like crystals | HCl |
| 60 | —NHCH$_3$ | —CH(CH$_3$)—CH=CH$_3$ | C$_2$H$_5$ | H | H | 169–170 (decomp.) (Ethanol-ether) | Colorless flake-like crystals | HCl |
| 61 | —NHCH$_3$ | —C$_2$H$_5$ | CH$_3$ | H | H | 175.5–176.5 (Ethanol-ether) | Colorless flake-like crystals | HCl |

EXAMPLE 62

1.77 Grams of 1-amino-7-hydroxy-4,6-dimethylindane and 50 ml of ethanol solution containing 2.57 g of 3,5-di-tert-butyl-4-hydroxybenzaldehyde were stirred together at a room temperature for 2 hours. Then sodium borohydride solution was added gradually by small portions to the reaction mixture under an ice-cooling condition. The reaction mixture was further stirred at a room temperature for 2 hours, then was acidified by adding hydrochloric acid. Then the reaction mixture was concentrated to dryness by evaporating the solvent under a reduced pressure. To the residue obtained was added 100 ml of water, and further added an aqueous solution of sodium acetate to adjust the pH of the solution to about pH=8, then extracted with 100 ml of ethyl acetate. The extract was washed with water, dried with anhydrous magnesium sulfate, concentrated to dryness by evaporating the solvent under a reduced pressure. The residue obtained was dissolved in 50 ml of ethanol, and the pH of the solution was adjusted by adding ethanol saturated with hydrogen chloride gas to about pH=3, then the solution was concentrated to dryness by evaporating the solvent under a reduced pressure. The residue obtained was recrystallized from ether-n-hexane to obtain 0.77 g of 1-(3,5-di-tert-butyl-4-hydroxybenzyl)amino-4,6-dimethyl-7-hydroxyindane in the form of colorless needle-like crystals. Melting point: 154°–155° C.

By a method similar to that described in Example 59 compounds of Examples 38–41 and 43–49 were prepared.

EXAMPLE 63

5 Grams of 1-amino-4-methyl-6-α-chloroacetylaminomethyl-7-hydroxyindane hydrochloride and 100 ml of ethanol containing 50 ml of concentrated hydrochloric acid were refluxed by heating for 8 hours. The solvent was removed by evaporation and the residue obtained was washed with ethanol. Recrystallized from methanol-ether to obtain 1 g of 1-aminomethyl-6-aminomethyl-7-hydroxyindane dihydrochloride.

Colorless powdery substance
Melting point: 220° C. (decomp.)

Example of injection preparation

| 7-Hydroxy-4-methyl-1-indanone oxime | 200 mg |
|---|---|
| Glucose | 250 mg |
| Distilled water for injection | q.s. |
| Total | 5 ml |

7-Hydroxy-4-methyl-1-indanone oxime and glucose were dissolved in distilled water for injection, the solution was filled in an ampule of 5 ml volume. After the air in the filled ampule was replaced with nitrogen gas, the ampule was sterilized with steam under pressure at 121° C. for 15 minutes to obtain the injection preparation having the above-mentioned formulation.

Example of film coated tablets preparation

| 1-Amino-7-hydroxy-4-methylindane hydrochloride | 100 g |
|---|---|
| Avicel (a trademark for microcrystalline cellulose, manufactured by Asahi Chemical Industry Co., Ltd.) | 40 g |
| Corn starch | 30 g |
| Magnesium stearate | 2 g |
| TC-5 (a trademark for hydroxypropyl methylcellulose, manufactured by The Shin-Etsu Chemical Co., Ltd.) | |
| Polyethylene glycol-6000 | 3 g |
| Castor oil | 40 g |
| Methanol | 40 g |

1-Amino-7-hydroxy-4-methylindane hydrochloride, Avicel, corn starch and magnesium stearate were admixed together and ground, then the mixture obtained was shaped into tablets by using a tablet machine (R 10 mm). The tables obtained were cotaed with a film coating consisting of TC-5, polyethylene glycol-6000, castor oil and methanol to prepare the film coated tablets having the above-mentioned formulation.

Example of ointment preparation

| 1-Amino-4,6-dichloro-7-hydroxyindane hydrochloride | 2 g |
|---|---|
| Purified lanolin | 5 g |
| White bees wax | 5 g |
| White petrolatum | 88 g |
| Total | 100 g |

White bees wax was warmed to make it a liquid state, then 1-amino-4,6-dichloro-7-hydroxyindane, purified lanolin and white petrolatum were added therein. The mixture was warmed to make it liquid state, then stirred until solidified to prepare the ointment having the above-mentioned formulation.

PHARMACOLOGICAL TESTS

1. Test compounds (1) Compounds of the present invention

I. 1-Amino-7-hydroxy-4-methylindane hydrochloride
II. 1-Amino-7-hydroxy-4,6-dimethylindane hydrochloride
III. 1-Amino-7-hydroxy-4-methyl-6-iodoindane hydrochloride
IV. 1-Amino-7-hydroxy-4,6-dichloroindane hydrochloride
V. 1-Methylamino-4,6-dimethyl-7-hydroxyindane hydrochloride
VI. 1-Amino-2,2,4,6-tetramethyl-7-hydroxyindane hydrochloride
VII. 1-Amino-4-methyl-6-sec-butyl-7-hydroxyindane hydrochloride
VIII. 1-Amino-4-methyl-6-iso-butyl-7-hydroxyindane hydrochloride
IX. 1-Amino-4-methyl-6-n-propyl-7-hydroxyindane hydrochloride
X. 1-n-Butylamino-4,6-dimethyl-7-hydroxyindane hydrochloride
XI. 1-Amino-4-methyl-6-bromo-7-hydroxyindane hydrobromide
XII. 1-Amino-4-methyl-6-nitro-7-hydroxyindane hydrochloride
XIII. 1-Amino-6-n-propyl-7-hydroxyindane hydrochloride
XIV. 1-Methylamino-4-methyl-6-methylthio-7-hydroxyindane hydrochloride
XV. 1-Methylamino-4-ethyl-6-(1-methyl-2-propenyl)7-hydroxyindane hydrochloride
XVI. 1-Amino-4-ethyl-6-n-propyl-7-hydroxyindane hydrochloride
XVII. 1-Methylamino-4-ethyl-6-methyl-7-hydroxyindane hydrochloride
XVIII. 1-Methylamino-4-methyl-6-ethyl-7-hydroxyindane hydrochloride
XIX. 1-Amino-4-ethyl-6-sec-butyl-7-hydroxyindane hydrochloride
XX. 1-Methylamino-4-ethyl-6-allyl-7-hydroxyindane hydrochloride
XXI. 4,6-Dimethyl-7-hydroxy-1-indanone oxime (2) Reference compounds
BHT: Butylhydroxytoluene
VE: Vitamin E Pharmacological test—1

Oxidation inhibitory activity test (in vitro test)

Luminol (5-amino-2,3-dihydro-1,4-phthalazinedione) is known as a chemoluminescent which shows a strong chemoluminescence when it is reacted with hydrogen peroxide in the presence of hemin as a catalyst.

This test was conducted to know the oxidation inhibitory activity of a test compound (as an oxidation inhibitor) by determining the inhibitory degree of oxidation of luminol with linoleic acid hydroperoxide (which is known as a strong oxidizing agent similarly as hydrogen peroxide) affected by the test compound.

In this test, vitamin E was used as one of the reference compounds. On the basis of its oxidation inhibitory activity, vitamin E is known as a compound enabling to lower the concentration of peroxidized lipid in the blood which is induced by the action of alloxane in vivo. A compound having such an oxidation inhibitory activity similar to vitamin E can be recognized as an oxidation inhibitor which can be expected to have an ability for lowering the concentration of peroxidized lipid in the blood.

1. Method for the test (1) Test solutions

A methanol solution containing 1.0 to $1.0 \times 10^{-6}$ mg/ml of a test compound and $1.0 \times 10^{-9}$ mol/ml of linoleic acid hydroperoxide (hereafter referred to as "Test compound solution") was prepared.

On the other hand, 0.1 M-sodium carbonate buffer solution containing $1.0 \times 10^{-4}$ M of luminol (hereafter referred to as "Luminol solution"), and 0.1 M-sodium carbonate buffer solution containing $1.25 \times 10^{-6}$ g/ml of FCS (a fetal calf serum, manufactured by Gibco & Co.) (hereafter referred to as "FCS solution") were prepared respectively.

(2) Test apparatus

In conducting this test, a test apparatus having the flow system as shown in the accompanying FIG. 1 was used. In FIG. 1, wherein numeral (1) is a photocounter, numeral (2) is a cell, numeral (3) is a mixer, numeral (4) is a Test compound solution, numeral (5) is a Luminol solution (chemoluminescent solution), numeral (6) is a FCS solution (a catalyst solution), numeral (7) is 0.1 M-sodium carbonate buffer solution (a buffer solution for washing), numeral (8) is a syrings, numeral (9) is a bottle for receiving the drainage, and numeral (10) is a stop-valve.

(3) Test procedure

Into the test apparatus having the flow system indicated in FIG. 1, 0.4 ml each of Test compound solution, FCS solution and Luminol solution were sucked and admixed automatically in this order. Afeer admixing with Luminol solution at the last stage, the chemoluminescene emitted from the cell (2) was measured for 1 second by using a photocounter (1) (Photocunter R649S, manufactured by Hamamatsu Photonics & Co.).

The test was conducted by using each of Test compound solutions containing various concentrations of the test compound respectively as shown in Table 2. The amount of emitted hhemoluminescence measured with respect to each of Test compound solution having predetermined concentration of the test compound are also indicated in Table 2.

(4) Test results—1

The amount of chemoluiinescence (%) of the respective test compound is calculated in terms of percent on the basis of the amount obtained from a Test compound solution containing no test compound as 1.0, and calculated from the following formula.

$$\text{Amount of chemoluminescence (\%)} = \frac{C - B}{A - B} \times 100$$

wherein

A = count of chemoluminescence of Test compound solution containing no test compound, but containing linoleic acid hydroperoxide B = count of chemoluminescence of Test compound solution containing neither test compound nor linoleic acid hydroperoxide C = count of chemoluminescence of Test compound solution containing both test compound and linoleic acid hydroperoxide The results of the test are shown in Table 7.

TABLE 7

| Concentration of test compound (mg/ml) | Amount of chemoluminescence (%) | | | | | |
|---|---|---|---|---|---|---|
| | I | II | III | IV | BHT | VE |
| 1.0 | 2.0 | — | — | 51 | — | 15.5 |
| $1.0 \times 10^{-1}$ | 2.0 | 0.3 | 18.0 | 95 | 0.8 | 64.6 |
| $1.0 \times 10^{-2}$ | 6.0 | 2.3 | 50.0 | — | 22 | 81.0 |
| $1.0 \times 10^{-3}$ | 52.0 | 4.4 | 85.0 | — | 53 | — |
| $1.0 \times 10^{-4}$ | — | 39 | — | — | — | — |

(5) Test results—2

By a method similar to that described in the above test, $IL_{50}$ (50% inhibitory activity) of both the test compounds and the reference compounds against the oxidative ability of $1.0 \times 10^{-9}$ mol/ml of linoleic acid hydroperoxide solution (5 μl) were measure in terms of the concentration of the test compound. The results are shown in Table 8.

TABLE 8

| Test compound | $IL_{50}$ (mg/ml) |
|---|---|
| I | $1.12 \times 10^{-3}$ |
| II | $1.0 \times 10^{-4}$ or more |
| III | $1.0 \times 10^{-2}$ |
| IV | 1.0 |
| BHT | $1.27 \times 10^{-3}$ |
| VE | $4.7 \times 10^{-1}$ |

As can be seen from the test results as shown in Table 7 and 8, indane derivatives (for example, test compounds I, II, III and IV) of the present invention clearly show oxidation inhibitory activities. Furthermore, indane derivatives of the present invention show strong oxidation inhibitory activities in vivo similar to those of shown by BHT and vitamin E as shown below animal tests.

Pharmacological test—2

Anti-inflammotory effects on carrageenin induced-edema

Male Wister-strain rats (weighing about 150 g body weight) were usdd as test animals. Five (5) rats were used as one test group. The rats were deprived of food for 18 hours, then feeded for 1 hour, and a test compound was orally administered at the rate of 100 mg/kg. One hour after the aministration, 0.1 ml of 1%-carrageenin solution was injected to the left hind leg of the rat, and the volume of the left hind leg was measured at 3 hours after the injection.

Swelling rate of the left hind leg ismmeasured as a percent (%) of the increased volume of the left hind leg after the injection of carrageenin solution over the volume of the left hind leg before the injectinn. Anti-inflammatory rate (%) is calculated from the mean values of the swelling rate obtained from the test group using test compound and the mean values obtained from the control group. The test results as shown in Table 9 as follows.

TABLE 9

| Test compound | Anti-inflammatory rate (%) |
|---|---|
| II | 77 |
| III | 76 |
| XXI | 38 |

Pharmacological test—3

Survival test under hypoxic condition

This test was conducted by a procedure similar to that described in "Arch. Int. Pharmacodyn. Ther., Vol. 233, page 137 (1978)".

ICR-strain male mice (weighing 20 to 30 g) were used as test animals. Four mice were used as one test group, the mice were placed in a glass desiccator with which a stop valve is equipped. Inside pressure of the desiccator was reduced until 210 or 240 mmHg by sucking the air by using a vacuum pump, then the stop valve was closed.

Survival time of the test mouse was determined as a length of time between the beginning of the vacuum pump operation and the cease of breathing of the mouse. A test compound was injected subcutaneously or intraperitoneally to the mouse at 15 minutes before the beginning of the vacuum pump operation.

In the case that the test mouse survived for over 30 minutes (under the pressure at 210 mmHg) was defined as survived for 30 minutes, similarly the test mouse survived for over 15 minutes (under the pressure at 240 mmHg) was defined as survived for 15 minutes.

The test results obtained from the test condition under the pressure at 210 mmHg are shown in Table 10, and the results obtained from the test condition under the pressure at 240 mmHg are shown in Table 11 as follows.

TABLE 10

| Test compound | Dose (mg/kg) | Method of administration | Survival time (sec.) | Number of test |
|---|---|---|---|---|
| Compound of the present invention | | | | |
| II | 10 | s.c. | 806.8 ± 181.7 | 10 |
|  | 30 | s.c. | 1189.0 ± 176.5 | 10 |
| III | 10 | s.c. | 1693.2 ± 106.8 | 10 |
|  | 30 | s.c. | 945.9 ± 251.5 | 10 |
| Control | — |  | 284.9 ± 21.5 | 30 |
| VI | 30 | s.c. | 484.2 ± 2 | 10 |
| XIII | 30 | s.c. | 210.9 ± 20.3 | 10 |
| XIV | 30 | s.c. | 1136.9 ± 227.5 | 10 |
| XV | 30 | s.c. | 251.3 ± 48.4 | 10 |
| XVI | 30 | s.c. | 394.3 ± 161.9 | 10 |
| XVII | 30 | s.c. | 575.9 ± 212.3 | 10 |
| XVIII | 30 | s.c. | 649.3 ± 171.7 | 10 |
| XIX | 30 | s.c. | 229.5 ± 19.3 | 10 |
| XX | 30 | s.c. | 259.5 ± 29.6 | 10 |
| Control | — | — | 165.9 ± 13.8 | 10 |
| VII | 30 | i.p. | 533.1 ± 170.0 | 10 |
| VIII | 30 | s.c. | 600.7 ± 147.7 | 10 |
| IX | 10 | i.p. | 851.0 ± 219.9 | 10 |
| X | 30 | s.c. | 370.3 ± 37.3 | 10 |
| XI | 30 | s.c. | 1191.4 ± 208.6 | 10 |
| Control | — | — | 214.5 ± 20.5 | 10 |
| V | 30 | s.c. | 452.5 ± 89.8 | 10 |
| XII | 30 | s.c. | 474.1 ± 116.4 | 10 |
| Control | — | — | 204.8 ± 44.2 | 10 |

TABLE 11

| Test compound | Dose (mg/kg) | Method of administration | Survival time (sec.) | Number of test |
|---|---|---|---|---|
| Compound of the present invention | | | | |
| I | 30 | s.c. | 657.2 ± 83.5 | 10 |
| II | 30 | s.c. | 828.1 ± 49.5 | 10 |
| III | 30 | s.c. | 889.3 ± 7.1 | 10 |
| Control | — | — | 481.3 ± 49.3 | 30 |

Pharmacological test—4

Survival test on cerabral hemorrhagic death induced by intraperitoneal administration of 50%-glucose saline solution This experiment was conduced by using 30 mice as one test group. Test compound II of the present invention was subcutaneously administered to individual mouse at the rate of 0.3, 1.0 and 33.0 mg/kg separately. 15 Minutes after the subuutaneous administration, then 50%-glucose saline solution (weight/volume of saline) was further administered intraperitoneally to the mouse at the rate of 0.4 m/10 g of body weight.

Survival rate of the mice was determined by the observation at the tim intervals of 1.5, 3.0 and 24 hours after the administration of 50%-glucose solution.

The effect of the respective dose of the test compound II in connection with the survival rate was checked by two sided test in accordance with method of Fisher's direct probability test. The results are shown in Table 12 as follwos.

TABLE 12

| | Survival rate (Time: hours) | | |
|---|---|---|---|
| Dose (mg/kg) (s.c.) | 1.5 | 3.0 | 24 |
| Reference | | | |
| Saline solution | 6/30 | 4/30 | 3/30 |
| Compound II of the present invention | | | |
| 0.3 mg/kg | 11/30 | 6/30 | 6/30 |
| 1.0 | 12/30 | 10/30 | 8/30 |
| 3.0 | 15/30 | 8/30 | 8/30 |

As can be seen from the above-mentioned various pharmacological tests results shown in Tables 7 to 12, indane derivatives of the present invention are useful prophylactics and treating agent for curing various symptoms and syndromes caused by peroxidized substances and active oxygen radicals formed in the living body. Furthermore, they are also useful as anti-inflamatory agents and other pharmaceutical applications.

What is claimed is:

1. Indane derivatives and their salts represented by the general formula (1),

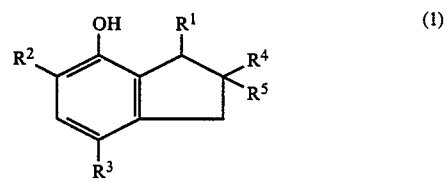

wherein $R^1$ is an amino group which may have lower alkyl groups as the substituents, a hydroxylimino group, an alkanoylamino group having 1 to 10 carbon atoms which may have halogen atoms as the substituents, a lower alkylsulfonylamino group, a phenylsulfonylamino group which may have lower alkyl groups as the substituents on the phenyl ring, a benzoylamino group having lower alkyl groups as the substituents on the phenyl ring, or a phenyl-lower alkylamino group having hydroxyl groups or lower alkyl groups as the substituents on the phenyl ring; $R^2$ is a hydrogen atom, a lower alkyl group, a halogen atom, a nitro group, an amino group, an amino-lower alkyl group, a lower alkanoylamino group, a lower alkanoylamino-lower alkyl group which may have halogen atoms as the substituents, a lower alkylthio group, a 1-piperidinesulfonyl group, or a lower alkenyl group; $R^3$ is a hydrogen atom, a lower alkyl group, or a halogen atom; $R^4$ and $R^5$ are the same or different from each other, and are each a hydrogen atom, or a lower alkyl group; provided that when $R^1$ is a hydroxylimino group, then both $R^2$ and $R^3$ should not be hydrogen atoms at the same time.

2. The indane derivatives and their salts according to claim 1, wherein $R^1$ is an amino group.

3. The indane derivatives and their salts according to claim 1, wherein $R^1$ is an alkylamino group having 1 to 6 carbon atoms.

4. The indane derivatives and their salts according to claim 1, wherein $R^1$ is a hydroxylimino group, an alkanoylamino group having 1 to 10 carbon atoms which may have halogen atoms as the substituents, an alkylsulfonylamino group having 1 to 6 carbon atoms, a phenylsulfonylamino group which may have alkyl groups having 1 to 6 carbon atoms as the substituents on the phenyl ring, a benzoylamino group having alkyl groups having 1 to 6 carbon atoms as the substituents on the phenyl ring, or a phenyl-$C_{1-6}$ alkylamino group having hydroxyl groups or alkyl groups having 1 to 6 carbon atoms on the phenyl ring.

5. The indane derivatives and their salts according to claim 2, wherein $R^2$ is a hydrogen, an alkyl group having 1 to 6 carbon atoms, a halogen atom or a nitro group; and $R^3$ is a hydrogen atom, an alkyl group having 1 to 6 carbon atom or a halogen atom.

6. The indane derivatives and their salts according to claim 2, wherein $R^2$ is an amino group, an aminoalkyl group having 1 to 6 carbon atoms, an alkanoylamino group having 1 to 6 carbon atoms, a $C_{1-6}$ alkanoylamino-$C_{1-6}$ alkyl group which may have halogen atoms as the substituents, an alkylthio group having 1 to 6 carbon atoms, 1-piperidinesulfonyl group, or an alkenyl group having 2 to 6 carbon atoms; and $R^3$ is a hydrogen atom, an alkyl group having 1 to 6 carbon atoms, or a halogen atom.

7. The indane derivatives and their salts according to claim 5, wherein $R^2$ and $R^3$ are alkyl groups having 1 to 6 carbon atoms.

8. The indane derivatives and their salts according to claim 7, wherein any one of $R^2$ and $R^3$ is an alkyl group having 1 to 6 carbon atoms, and the other one is an alkyl group having 2 to 6 carbon atoms.

9. The indane derivatives and their salts according to claim 7, wherein $R^2$ and $R^3$ are alkyl groups having 2 to 6 carbon atoms.

10. The indane derivatives and their salts according to claim 8, wherein at least one of $R^2$ and $R^3$ is a branched chain alkyl group having 3 to 6 carbon atoms.

11. The indane derivatives and their slts according to claim 9, wherein at least one of $R^2$ and $R^3$ is a branched chain-alkyl group having 3 to 6 carbon atoms.

12. The indane derivativss and their salts according to claim 8, wherein $R^2$ is a methyl group, and $R^3$ is an alkyl group having 2 to 6 carbon atoms.

13. The indane derivatives and their salts according to claim 12, wherein $R^2$ is a methyl group, and $R^3$ is a branched chain alkyl group having 3 to 6 carbon atoms.

14. The indane derivatives and their salts according to claim 8, wherein $R^2$ is an alkyl group having 2 to 6 carbon atoms, and $R^3$ is a methyl group.

15. The indane derivatives and their salts according to claim 14, wherein $R^2$ is a branched chain-alkyl group having 3 to 6 carbon atoms, and $R^3$ is a methyl group.

16. The indane derivatives and their salts according to claim 9, wherein any one of $R^2$ and $R^3$ is an ethyl group, and the other one is an alkyl group having 2 to 6 carbon atoms.

17. The indane derivatives and their salts according to claim 16, wherein any one of $R^2$ and $R^3$ is an ethyl group, and the other one is a branched chain-alkyl group having 3 to 6 carbon atoms.

18. The indane derivatives and their salts according to claim 3, wherein both $R^2$ and $R^3$ are alkyl groups having 1 to 6 carbon atoms.

19. 1-Amino-7-hydroxy-4-methyl-6-n-propylindane.

20. 1-Amino-7-hydroxy-4-methyl-6-(1-methylpropyl)indane.

21. 1-Amino-7-hydroxy-4-methyl-6-(2-methylpropyl)indane.

22. 1-Amino-7-hydroxy-4-ethyl-6-(1-methylpropyl)indane.

23. 1-Methylamino-7-hydroxy-4-ethyl-6-methylindane.

24. 1-Amino-7-hydroxy-2,2,4,6-tetramethylindane.

25. 1-Amino-7-hydroxy-4-ethyl-6-n-propylindane.

26. A pharmaceutical composition for improving anoxemic and hypoxic symptoms and syndromes accompanied therewith containing, as the active ingredient, n indane derivative or salt thereof represented by the general formula (1) as claimed in claim 1.

27. An antioxidizing composition containing, as the active ingredient, an indane derivative or salt thereof represented by theggeneral formula (1) as claimed in claim 1.

28. Indane derivatives and salts thereof represented by the general formula (1),

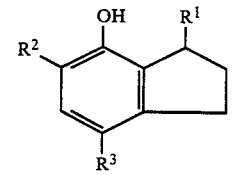

wherein $R^1$ is an amino group or a hydroxylimino group; $R^2$ and $R^3$ are the same or different and each is a hydrogen atom, a lower alkyl group or a halogen atom; provided that when $R^1$ is a hydroxylimino group then both $R^2$ and $R^3$ should not be hydrogen atoms at the same time.

29. The indane derivatives and salts thereof of claim 28 wherein $R^1$ is an amino group.

30. The indane derivatives and salts thereof of claim 29 wherein $R^2$ is a propyl group and $R^3$ is a methyl group.

31. The indane dervatives and salts thereof of claim 29 wherein $R^2$ is butyl group and $R^3$ is a methyl group.

32. The indane derivatives and salts thereof of claim 29 wherein $R^2$ is a butyl group and $R^3$ is an ethyl group.

33. The indane derivatives and salts thereof of claim 29 wherein $R^2$ is a methyl group and $R^3$ is an ethyl group.

34. The indane derivatives and salts thereof of claim 29 wherein $R^2$ and $R^3$ are both methyl groups.

35. The indane derivatives and salts thereof of claim 29 wherein $R^2$ is a propyl group and $R^3$ is an ethyl group.

* * * * *

UNITED STATES PATENT AND TRADEMARK OFFICE
CERTIFICATE OF CORRECTION

PATENT NO. : 4,792,628
DATED     : December 20, 1988
INVENTOR(S) : Yasuo Oshiro et al.

It is certified that error appears in the above-identified patent and that said Letters Patent is hereby corrected as shown below:

Column 45, claim 11, line 61, delete "slts" and insert --salts--; and claim 12, line 63, delete "derivativss" and insert --derivatives--.

Column 46, claim 26, line 30, delete "n indane" and insert --an indane--.

Signed and Sealed this

Sixteenth Day of May, 1989

Attest:

DONALD J. QUIGG

Attesting Officer

Commissioner of Patents and Trademarks